US011154520B2

(12) United States Patent
Glazier

(10) Patent No.: US 11,154,520 B2
(45) Date of Patent: Oct. 26, 2021

(54) COMBINATION THERAPY FOR METASTATIC CANCER

(71) Applicant: General Oncology, Inc., Newton, MA (US)

(72) Inventor: Arnold Glazier, Newton, MA (US)

(73) Assignee: General Oncology, Inc., Newton, MA (US)

(*) Notice: Subject to any disclaimer, the term of this patent is extended or adjusted under 35 U.S.C. 154(b) by 259 days.

(21) Appl. No.: 15/778,796

(22) PCT Filed: Dec. 6, 2016

(86) PCT No.: PCT/US2016/065079
§ 371 (c)(1),
(2) Date: May 24, 2018

(87) PCT Pub. No.: WO2017/100162
PCT Pub. Date: Jun. 15, 2017

(65) Prior Publication Data
US 2018/0338935 A1 Nov. 29, 2018

Related U.S. Application Data

(60) Provisional application No. 62/263,880, filed on Dec. 7, 2015.

(51) Int. Cl.
*A61K 31/375* (2006.01)
*A61K 31/714* (2006.01)
*A61K 31/198* (2006.01)
*A61P 35/04* (2006.01)
*A61K 31/17* (2006.01)
*A61K 45/06* (2006.01)
*A61K 31/045* (2006.01)

(52) U.S. Cl.
CPC .......... *A61K 31/17* (2013.01); *A61K 31/045* (2013.01); *A61K 31/198* (2013.01); *A61K 31/375* (2013.01); *A61K 31/714* (2013.01); *A61K 45/06* (2013.01); *A61P 35/04* (2018.01); *A61K 2300/00* (2013.01)

(58) Field of Classification Search
CPC ..... A61P 35/04; A61K 31/198; A61K 31/175; A61K 31/714; A61K 31/375
See application file for complete search history.

(56) References Cited

U.S. PATENT DOCUMENTS

| 5,639,787 A | 6/1997 | Riordan | |
|---|---|---|---|
| 2003/0212038 A1* | 11/2003 | Niyikiza | A61K 31/525 514/52 |
| 2009/0123447 A1* | 5/2009 | Choi | A61K 31/19 424/94.4 |
| 2012/0184609 A1* | 7/2012 | Jamison | A61K 31/185 514/474 |
| 2015/0265641 A1 | 9/2015 | Glazier | |
| 2018/0071328 A1 | 3/2018 | Glazier | |
| 2019/0240240 A1 | 8/2019 | Glazier | |

FOREIGN PATENT DOCUMENTS

| JP | 2003-501488 A | 1/2003 |
|---|---|---|
| JP | 2005-521053 A | 7/2005 |
| WO | WO 2000/076556 A2 | 12/2000 |
| WO | WO 2003/081238 A2 | 10/2003 |
| WO | 2004/043374 A2 | 5/2004 |
| WO | 2014/066400 A2 | 5/2014 |

OTHER PUBLICATIONS

MedicineNet ("Definition of Body Surface Area." (Dec. 26, 2014). https://web.archive.org/web/20141226025143/https://www.medicinenet.com/script/main/art.asp?articlekey=39851 (Year: 2014).*

LabChem performance through chemistry / Ascorbic Acid Safety Data Sheet according to Federal Register / vol. 77, No. 58 / Monday, Mar. 26, 2012 / Rules and Regulations (Dec. 6, 2016). (Year: 2016).*

Ahmad, I. et al., "Effect of Ascorbic Acid on the Degradation of Cyanocobalamin and Hydroxocobalamin in Aqueous Solution: A Kinetic Study," AAPS PharmSciTech, vol. 15; No. 5; 1324-1333 (2014).

Akatov, V.S. et al., "Combined Vitamins $B_{12b}$ and C Induce the Glutathione Depletion and the Death of Epidermoid Human Larynx Carcinoma Cells HEp-2," Bioscience Reports, vol. 20; No. 5; 411-417 (2000).

Arning. J. et al., "Structure-activity relationships for the impact of selected isothiazol-3-one biocides on glutathione metabolism and glutathione reductase of the human liver cell Hep G2," Toxicoloy, vol. 246; 203-212 (2008).

Babson, J.R. and Reed, D.J., "Inactivation of Glutathione Reductase by 2-Chloroethyl Nitrosourea-Derived Isocyanates," Biochemical and Biophysical Research Communications, vol. 83; No. 2; 754-762 (1978).

(Continued)

Primary Examiner — Jeffrey S Lundgren
Assistant Examiner — Chris E Simmons
(74) Attorney, Agent, or Firm — Hamilton, Brook, Smith & Reynolds, P.C.

(57) ABSTRACT

The present invention relates to methods and sets of drugs for the effective treatment of metastatic cancer and the administration of a set of drugs that overcome mechanisms of resistance to DNA-damaging agents, thereby sensitizing cancer cells to said DNA-damaging agents. The methods involve the administration of a set of drugs comprising melphalan, BCNU, hydroxocobalamin, and ascorbic acid. In a preferred embodiment, ethanol is also added to the set of drugs and bone marrow toxicity is reversed with an infusion of bone marrow stem cells. The methods also involve the depletion of GSH in tumors and the selective delivery of drugs to solid tumors. The methods also involve preventing the loss of catalase function and preventing oxidant-induced hemolysis and/or methemoglobin formation in subjects treated with oxidant drugs or agents that generate hydrogen peroxide, wherein said methods comprise the systemic administration of ethanol.

12 Claims, No Drawings

(56) References Cited

OTHER PUBLICATIONS

Bailey, H.H. et al., "Phase I Clinical Trial of Intravenous $_L$-Buthionine Sulfoximine and Melphalan: An Attempt at Modulation of Glutathione," J. Clin. Oncol., vol. 12; 194-205 (1994).

Bailey, H.H. et al., "Phase I Study of Continuous-Infusion $_L$-S,R-Buthionine Sulfoximine with Intravenous Melphalan," J. Natl Cancer Inst, vol. 89; 1789-1796 (1997).

Barron, C.C. et al., "Facilitative glucose transporters: Implications for cancer detection, prognosis and treatment," Metabolism Clinical and Experimental, vol. 65; 124-139 (2016).

Berger, S.J. et al., "Sensitive Enzymatic Cycling Assay for Glutathione: Measurements of Glutathione Content and Its Modulation by Buthionine Sulfoximine in Vivo and In Vitro in Human Colon Cancer," Cancer Research, vol. 54; 4077-4083 (1994).

Berry, D.A. et al., "High-Dose Chemotherapy With Autologous Hematopoietic Stem-Cell Transplantation in Metastatic Breast Cancer: Overview of Six Randomized Trials." Journal of Clinical Oncology, vol. 29; No. 24; 3224-3231 (2011).

Bhuyan, B.K. et al., "Multidrug Resistance Is a Component of V79 Cell Resistance to the Alkylating Agent Adozelesin," Cancer Research, vol. 53; 1354-1359 (1993).

Buehring, G.C. and Jensen, H.M., "Lack of Toxicity of Methylene Blue Chloride to Supravitally Stained Human Mammary Tissues," Cancer Research, vol. 43; 6039-6044 (1983).

Butryn, R.K et al., "V79 Chinese hamster lung cells resistant to the bis-alkylator bizelesin are multidrag-resistant," Cancer Chemother Pharmacol, vol. 34; 44-50 (1994).

Brynes, R.W., "Evidence for Involvement of Multiple Iron Species in DNA Single-Strand Scission by $H_2O_2$ in HL-60 Cells," Free Radical Biology & Medicine, vol. 20; No. 3; 399-406 (1996).

Canada, A. et al., "Glutathione depletion increases the cytotoxicity of melphalan to PC-3, an androgen-insensitive prostate cancer cell line," Cancer Chemother Pharmacol, vol. 32; 73-77 (1993).

Cao, P. et al., "The DNA Minor Groove-alkylating Cyclopropylpyrroloindole Drugs Adozelesin and Bizelesin Induce Different DNA Damage Response Pathways in Human Colon Carcinoma HCT116 Cells," Molecular Cancer Therapeutics, vol. 2; 651-659 (2003).

Carter, C.A. et al., "Preclinical Antitumor Activity of Bizelesin in Mice." Clinical Cancer Research, vol. 2; 1143-1149 (1996).

Chen, Q. et al., "Ascorbate in pharmacologic concentrations selectively generates ascorbate radical and hydrogen peroxide in extracellular fluid in vivo," PNAS, vol. 104; No. 21; 8749-8754 (2007).

Chen, Q. et al., "Pharmacologic doses of ascorbate act as a prooxidant and decrease growth of aggressive tumor xenografts in mince," PNAS, vol. 105; No. 32; 11105-11109 (2008).

Chresta, C.M. et al., "Depletion of Cellular Glutathione by N,N'-Bis(trans-4-Hydroxycyclohexyl)-N'-nitrosourea as a Determinant of Sensitivity of K562 Human Leukemia Cells to 4-Hydroperoxycyclophosphamide," Cancer Research, vol. 50; 4067-4071 (1990).

Colussi, G. et al., "$H_2O_2$-induced block of glycolysis as an active ADP-ribosylation reaction protecting cells from apoptosis," FASEB J., vol. 14; 2266-2276 (2000).

Coombes, R.C. et al., "High dose chemotherapy and autologous stem cell transplantation as adjuvant therapy for primary breast cancer patients with four or more lymph nodes involved: long-term results of an international randomized trial," Annals of Oncology, vol. 16; 726-734 (2005).

Cornbleet, M.A. et al., "Treatment of advanced malignant melanoma with high-dose melphalan and autologous bone marrow transplantation," Br. J. Cancer, vol. 48; 329-334 (1983).

Cornbleet. M.A. et al., "High-Dose Alkylating Agent Therapy: A Review of Clinical Experiences," Cancer Drug Delivery, vol. 1; No. 3; 227-238 (1984).

Deponte, M. et al., "Mechanistic Studies on a Novel, Highly Potent Gold-Phosphole Inhibitor of Human Glutathione Reductase," The Journal of Biological Chemistry, vol. 280; No. 21; 20628-20637 (2005).

Du, J. et al., "Ascorbic acid: Chemistry, biology and the treatment of cancer," Biochimica et Biophysica Acta, vol. 1826; 443-457 (2012).

Duarte, T.L. and Jones, G.D.D., "Vitamin C modulation of $H_2O_2$-induced damage and iron homeostasis in human cells," Free Radical Biology & Medicine, vol. 43; 1165-1175 (2007).

Dubler, R.E. and Anderson, B.M., "Simultaneous inactivation of the catalytic activities of yeast glutathione reductase by N-alkylmaleimides," Biochimica et Biophysica Acta, vol. 659; 70-85 (1981).

Evers, B. et al., "A High-Throughout Pharmaceutical Screen Identifies Compounds with Specific Toxicity against BRCA2-Deficient Tumors," Clin Cancer Research, vol. 16; No. 1; 99-108 (2010).

Feldman, D.R. et al., "TI-CE High-Dose Chemotherapy for Patients with Previously Treated Germ Cell Tumors: Results and Prognostic Factor Analvsis," Journal of Clinical Oncology, vol. 28; No. 10; 1706-1713 (2010).

Fitzgerald, G.B et al., "2,4-dihydroxybenzylamine: A specific inhibitor of glutathione reductase." Biochemical Pharmacology, vol. 41; No. 2; 185-190 (1991).

Frei III. E. et al., "Preclinical Studies and Clinical Correlation of the Effect of Alkylating Dose," Cancer Research, vol. 48; 6417-6423 (1988).

Friedman, H.S. et al., "Phase I Trial of Carmustine Plus $O^6$-Benzvlguanine for Patients with Recurrent or Progressive Malignant Glioma." J. Clin. Oncol., vol. 18; 3522-3528 (2000).

Frischer, H. and Ahmad, T., "Severe generalized glutathione reductase deficiency after antitumor chemotherapy with BCNU [1,3-bis(chloroethyl)-1-nitrosourea]," J Lab Clin Med., vol. 89; No. 5; 1080-1091 (1977).

Gosland, M.P. et al., "Reversal by Ccfopcrazonc of Resistance of Etoposide, Doxorubicin, and Vinblastine in Multidrug Resistant Human Sarcoma Cells." Cancer Research, vol. 49; 6901-6905 (1989).

Green, J.A. et al., "Potentiation of Melphalan Cytotoxicity in Human Ovarian Cancer Cell Lines by Glutathione Depletion," Cancer Research, vol. 44: 5427-5431 (1984).

Hanrahan, E.O. et al., "Randomized Trial of High-Dose Chemotherapy and Autologous Hematopoietic Stem Cell Support for High-Risk Primary Breast Carcinoma," Cancer, vol. 106; 2327-2336 (2006).

Hoffer, L.J. et al., "Phase I clinical trial of i.v. ascorbic acid in advanced malignancy," Annals of Oncology, 6 pages (2008).

Hucl, T. et al., "A Syngeneic Variance Library for Functional Annotation of Human Variation: Application of BRCA2," Cancer Research, vol. 68; No. 13; 5023-5030 (2008).

Jevtorić-Todorović, V. and Guenthner, T.M., "Sensitization of human melanoma cells to melphalan cytotoxicity by Adriamycin and carmustine," J Cancer Res Oncol., vol. 117; 313-320 (1991).

Jevtorić-Todorović, V. and Guenthner, T.M., "Depletion of a Discrete Nuclear Glutathione Pool by Oxidative Stress, But Not by Buthionine Sulfoximine," Biochemical Pharmacology, vol. 44; No. 7; 1383-1393 (1992).

Jochheim, C.M. and Baillie, T.A., "Selective and Irreversible Inhibition of Glutathione Reductase in Vitro by Carbamate Thioester Conjugates of Methyl Isocyanate," Biochemical Pharmacology, vol. 47; No. 7; 1197-1206 (1994).

Karplus, P.A. et al., "Inhibition of human glutathione reductase by the nitrosourea drugs 1,3-bis(2-chloroethyl)-1-nitrosourea and 1-(2-chloroethyl)-3-(2-hydroxyethyl)-1-nitrosourea," Eur. J. Biochem, vol. 171; 193-198 (1988).

Kassahun, K. et al., "Effect of Carbamate Thioester Derivatives of Methyl- and 2-chloroethyl Isocyanate on Glutathione Levels and Glutathione Reductase Activity in Isolated Rat Hepatocytes," Biochemical Pharmacology, vol. 48; No. 3; 587-594 (1994).

Kelner, M. J. and Alexander, N.M., "Methylene Blue Directly Oxidizes Glutathione without the Intermediate Formation of Hydrogen Peroxide," The Journal of Biological Chemistry, vol. 260; No. 28; 15168-15171 (1985).

Keshari, K.R. et al., "Hyperpolarized $^{13}$C dehydroascorbate as an endogenous redox sensor for in vivo metabolic imaging," PNAS, vol. 108; No. 46; 18606-18611 (2011).

(56) References Cited

OTHER PUBLICATIONS

Kirkman, H.N. et al., "The Function of Catalase-bound NADPH," The Journal of Biological Chemistry, vol. 262; No. 2; 660-666 (1987).
Kirkman, H.N. et al., "Mechanisms of Protection of Catalase by NADPH," The Journal of Biological Chemistry, vol. 274; No. 20; 13908-13914 (1999).
Kovach, J.S. et al., "A controlled study of combined 1,3-bis(2-chloroethyl)-1-nitrosourea and 5-fluorouragil therapy for advanced gastric and pancreatic cancer," vol. 33; 563-567 (1974).
Kurz, T. et al., "Lysosomal Redox-Active Iron Is Important for Oxidative Stress-Induced DNA Damage," Ann. N.Y. Acad. Sci., vol. 1019; 285-288 (2004).
Lacagnin, L.B. et al., "Metabolic changes in alveolar type II cells after exposure to hydrogen peroxide," Am J Physiol., L57-L65 (1990).
Lakhani, S. et al., "Chemotherapy for malignant melanoma: combinations and high doses produce more responses without survival benefit," Br. J. Cancer, vol. 61; 330-334 (1990).
Lazarus, H.M. et al., "Intensive Melphalan Chemotherapy and Cryopreserved Autologous Bone Marrow Transplantation for the Treatment of Refractory Cancer." Journal of Clinical Oncology, vol. 1; No. 6; 359-367 (1983).
Liu. X. and Sturla, S., "Profiling patterns of glutathione reductase inhibition by the natural product illudin S and its acylfulvene analogues," Mol Biosyst., vol. 5; No. 9; 1013-1024 (2009).
May, J.M. et al., "Generation of oxidant stress in cultured endothelial cells by methylene blue: protective effects of glucose and ascorbic acid," Biochemical Pharmacology, vol. 66; 777-784 (2003).
Monti, D.A. et al., "Phase I Evaluation of Intravenous Ascorbic Acid in Combination with Gemcitabine and Erlotinib in Patients with Metastatic Pancreatic Cancer." PLOS One, vol. 7; No. 1; E29794; 7 pages (2012).
Murray, D. and Meyn, R.E., "Effect of misonidazole pretreatment on nitrogen mustard-induced DNA cross-linking in mouse tissues in vivo," Br. J. Cancer, vol. 50; 801-808 (1984).
Nakamura, J. et al., "Micromolar concentrations of hydrogen peroxide induce oxidative DNA lesions more efficiently than millimolar concentrations in mammalian cells," Nucleic Acids Research, vol. 31; No. 6; 1790-1795 (2003).
Nathan, C.F. et al., "Tumor Cell Anti-Oxidant Defenses," J. Exp. Med., vol. 153; 766-782 (1980).
Nathan, C.F. and Cohn, Z.A., "Antitumor Effects of Hydrogen Peroxide in Vivo" J. Exp. Med., vol. 154; 1539-1553 (1981).
Nazhat, N.B. et al., "Destruction of Vitamin $B_{12}$ by Reaction with Ascorbate: The Role of Hydrogen Peroxide and the Oxidation State of Cobalt," Journal of Inorganic Biochemistry, vol. 36; 75-81 (1989).
Peters, W.P. et al., "Prospective, Randomized Comparison of High-Dose Chemotherapy With Stem-Cell Support Versus Intermediate-Dose Chemotherapy After Surgery and Adjuvant Chemotherapy in Women With High-Risk Primary Breast Cancer: A Report of CALGB 9082, SWOG 9114; and NCIC MA-13," Journal of Clinical Oncology, vol. 23; No. 10; 2191-2200 (2005).
Pierson, H.F. et al., "Depletion of Extracellular Cysteine with Hydroxocobalamin and Ascorbate in Experimental Murine Cancer Chemotherapy," Cancer Research, vol. 45; 4727-4731 (1985).
Pitot, H.C. et al., "A Phase I Study of Bizelesin (NSC 615291) in Patients with Advanced Solid Tumors," Clinical Cancer Research, vol. 8; 712-717 (2002).
Porrata, L.F. and Adjei, A.A., Tire pharmnacologic basis of high dose chemotherapy with haematopoietic stem cell support for solid tumors, British Journal of Cancer, vol. 85; No. 4; 484-489 (2001).
Rajan, A. et al., "A Phase I Combination Study of Olaparib with Cisplatin and Gemcitabine in Adults with Solid Tumors," Clinical Cancer Research, vol. 18; No. 8; 2344-2351 (2012).
Robey, R.W. et al., "Inhibition of P-glycoprotein (ABCB1)- and multidrug resistance-associated protein 1 (ABCC1)-mediated transport by the orally administered inhibitor, CBT-1®," Biochem Pharmacol., vol. 75; No. 6; 1302-1312 (2008).

Samuels, B.L. and Bitran, J.D., "High-Dose Intravenous Melphalan: A Review," J. Clin. Oncol., vol. 13; 1786-1799 (1995).
Sarosy, G. et al., "The Systemic Administration of Intravenous Melphalan." J. Clin. Oncol., vol. 6; 1768-1782 (1988).
Schwartz, G.H. et al., "A phase I study of bizelisin, a highly potent and selective DNA-interactive agent, in patients with advanced solid malignancies," Annals of Oncology, vol. 14; 775-782 (2003).
Seefeldt, T. et al., "Characterization of a Novel Dithiocarbamate Glutathione Reductase Inhibitor and Its Use as a Tool to Modulate Intracellular Glutathione," The Journal of Biological Chemistry, vol. 284; No. 5; 2729-2737 (2009).
Sirohi, B. et al., "An elective single autograft with high-dose melphalan: single-center study of 451 patients," Bone Marrow Transplantation, vol. 36; 19-24 (2005).
Smith, D.B. et al., "Phase II Evaluation of Melphalan in Adenocarcinoma of the Pancreas," Cancer Treatment Reports, vol. 69; No. 7-8; 917-918 (1985).
Solovieva, M.E. et al., "Vitamin $B_{12b}$ increases the cytotoxicity of short-time exposure to ascorbic acid, inducing oxidative burst and iron-dependent DNA damage," European Journal of Pharmacology, vol. 566; 206-214 (2007).
Spielholz, C. et al., "Increased Facilitated Transport of Dehydroascorbic Acid without Changes in Sodium-dependent Ascorbate Transport in Human Melanoma Cells," Cancer Research, vol. 57; 2529-2537 (1997).
Spitzer, G. et al., "High-Dose Chemotherapy With Autologous Bone Marrow Transplantation," Cancer, vol. 54; 1216-1225 (1984).
Stadtmauer, E.A. et al., "Conventional-Dose Chemotherapy Compared with High-Dose Chemotherapy Plus Autologous Hematopoietic Stem-Cell Transplantation for Metastatic Breast Cancer," The New England Journal of Medicine, vol. 342; No. 15; 1069-1076 (2000).
Stephenson, C.M. et al., "Phase I clinical trial to evaluate the safety, tolerability, and pharmacokinetics of high-dose intravenous ascorbic acid in patients with advanced cancer," Cancer Chemother Pharmacol., vol. 72; 139-146 (2013).
Tallman, M.S. et al., "Conventional Adjuvant Chemotherapy with or without High-Dose Chemotherapy and Autologous Stem-Cell Transplantation in High-Risk Breast Cancer," The New England Journal of Medicine, vol. 349; No. 1; 17-26 (2003).
Welsh, J.L. et al., "Pharmacological ascorbate with gemcitabine for the control of metastatic and node-positive pancreatic cancer (PACMAN): results from a phase I clinical trial," Cancer Chemother Pharmacol, vol. 71; 765-775 (2013).
Wilson, M.K. et al., "Review of high-dose intravenous vitamin C as an anticanccr agent," Asia-Pacific Journal of Clinical Oncology, vol. 10; 22-37 (2014).
Yu, M. et al., "Reversal of ATP-binding cassette drug transporter activity to modulate chemoresistance: why has it failed to provide clinical benefit?," Cancer Metastasis Rev, DOI 10.1007/s10555-012-9402-8; 17 pages (2012).
Yun, J. et al., "Vitamin C selectively kills KRAS and BRAF mutant colorectal cancer cells by targeting GAPDH." Science, vol. 350: No. 6266; 1391-1396 (2015).
Zander, A.R. et al., "High-Dose Chemotherapy with Autologous Hematopoietic Stem-Cell Support Compared with Standard-Dose Chemotherapy in Breast Cancer Patients with 10 or More Positive Lymph Nodes: First Results of a Randomized Trial," Journal of Clinical Oncology, vol. 22; No. 12; 2273-2283 (2004).
Child, J.A., et al., "High-Dose Chemotherapy with Hematopoietic Stem-Cell Rescue for Multiple Myeloma," The New England Journal of Medicine, vol. 348; No. 19; 1875-1883 (2003).
Dasgupta, R. et al., "Underactive Genetic Variants of Glutathione S-Transferase P1 (GSTP1) Modulate Survival in Multiple Myeloma," Blood, vol. 98; No. 11; 161a; Abstract #680 (2001).
Denz, U. et al., "State of the art therapy in multiple myeloma and future perspectives," European Journal of Cancer, vol. 42; No. 11; 1591-1600 (2006).
Fielder, K. and Durie, B.G.M., "Primary Amyloidosis Associated with Multiple Myeloma Predictors of Successful Therapy," American Journal of Medicine, vol. 80; No. 3; 413-418 (1986).

(56) References Cited

OTHER PUBLICATIONS

Peest, D. et al., "Melphalan and Prednisone (MP) versus Vincristine, BCNU, Adriamycin, Melphalan and Dexamethasone (VBAMDex) Therapy for Multiple Myeloma," Onkologie, vol. 13; No. 4; 43-44 (1990).

Poydock, M.E and Rice, D.R.J., "Influence of Vitamins C and B12 on the Survival Rate of Mice Bearing Ascites Tumor," Experimental Cell Biology, vol. 50; No. 2; 88-91 (1982).

Poydock, M.E. et al., "Growth-inhibiting effect of hydroxocobalamin and L-ascorbic acid on two solid tumors in mice," Elsevier Science Publishers, Database Embase [online]; accession No. EMB-1984201428; 1 page; Abstract (1984).

Poydock, M.E., "Effect of combined ascorbic acid and B-12 on survival of mice with implanted Ehrlich carcinoma and L1210 leukemia," The American Journal of Clinical Nutrition, vol. 54; No. 6; 1261S-1265S (1991).

Notification Concerning Transmittal of the International Preliminary Report on Patentability for International Application No. PCT/US2013/066200, entitled: "Methods for the Effective Treatment of Metastatic Cancer," dated May 7, 2015.

Notification of Transmittal of The International Search Report and the Written Opinion of the International Searching Authority for International Application No. PCT/US2013/066200, entitled: "Methods for the Effective Treatment of Metastatic Cancer," dated Nov. 17, 2014.

Notification Concerning Transmittal of The International Preliminary Report on Patentability for International Application No. PCT/US2016/065079, entitled: "Combination For The Effective Treatment Of Metastatic Cancer In Patients," dated Jun. 21, 2018.

Notification of Transmittal of The International Search Report and the Written Opinion of the International Searching Authority for International Application No. PCT/US2016/065079, entitled: "Combination For The Effective Treatment Of Metastatic Cancer In Patients," dated Apr. 24, 2017.

Akatov, V.S. et al., "Oxidative Stress in Hep-2 Human Laryngeal Carcinoma Cells Induced by Combination of Vitamins B12b and C," Bulletin of Experimental Biology and Medicine, vol. 136; No. 3; 279-282 (2003),.

Poydock, M.E. et al., "Growth-inhibiting effect of hydroxocobalamin and L-ascorbic acid on two solid tumors in mice," IRCS Med. Sci., vol. 12; 813 (1984).

Chen. A.I. et al., "Tandem chemo-mobilization followed by high-dose melphalan and carmustine with single autologous hematopoietic cell transplantation for multiple myeloma," Bone Marrow Transplantation, vol. 47; No. 4; 516-521 (2012).

* cited by examiner

COMBINATION THERAPY FOR METASTATIC CANCER

RELATED APPLICATIONS

This application is the U.S. National Stage of International Application No. PCT/US2016/065079, filed Dec. 6, 2016, which designates the U.S., published in English, and claims the benefit of U.S. Provisional Application No. 62/263,880, filed on Dec. 7, 2015. The entire teachings of the above applications are incorporated herein by reference.

BACKGROUND

Combination chemotherapy has given high cure rates for certain types of metastatic cancer, such as childhood leukemia, lymphoma, and testicular cancer. However, most common types of metastatic cancer are currently incurable. The 5-year survival rates of some metastatic cancers are approximately as follows: cervical 16%, colorectal 12.5%, uterine 16%, esophageal 3.5%, kidney 12.3%, liver/biliary 3%, lung/bronchus 3.9%, melanoma 16.1%, ovarian 27.3%, pancreatic 2%, stomach 3.9%, bladder 5.4%, breast 24.3%. The following references relate to this matter and are hereby incorporated in their entirety by reference: Frei E 3rd., Curative cancer chemotherapy, Cancer Res. 1985; 45:6523-37; Howlader N, et al., SEER Cancer Statistics Review, 1975-2010, National Cancer Institute. Bethesda, Md.). Despite decades of research and hundreds of billions of dollars, the age-adjusted cancer mortality rates reported by the U.S. National Cancer Institute for many types of cancers showed no decline over a 35-year period, from 1975-2010. During the same period, the National Library of Medicine catalogued 2,143,002 scientific articles about cancer, of which 112,429 related to the treatment of metastatic cancer, and since the 1950's there have been over 22,300 medical papers and scientific reports published on clinical trials for metastatic cancer and over 152,000 scientific papers published on combination cancer therapy. Despite this truly massive scientific effort, obtaining complete responses (CRs) —that is, the absence of all detectable cancer—in patients with most types of metastatic cancer has not been possible. Generally, a 99% or 2-log reduction in cancer cell burden is needed to obtain a CR. A patient with metastatic cancer can have tens of billions of cancer cells distributed throughout his or her body: decreasing the tumor cell burden by 2 logs would still leave millions to billions of viable cancer cells in the patient; with time those cancer cells could multiply and cause progressive disease. For example, the CR rate in pancreatic cancer using FOLFIRINOX, the most effective chemotherapy, is only 0.6%. In patients with metastatic melanoma treated with Nivolumab plus ipilimumab, the state-of-the-art therapy, the CR rate was 9.6%. The CR rate in patients with melanoma treated with the BRAF inhibitor Vemurafenib was 1%. Similar low rates of CRs are seen with most types of metastatic cancers. Durable, long-term CRs are even rarer in patients with most types of metastatic disease. The following references relate to this matter and are hereby incorporated in their entirety by reference: Conroy T, et al., N Engl J Med., 2011 May 12, 364(19):1817-25; Wolchok J D, et al., N Engl J Med., 2013 Jul. 11, 369(2):122-33; Chapman P B, et al., N Engl J Med., 2011 Jun. 30, 364(26):2507-16. There have been thousands of clinical trials with a large number of different combinations of anticancer drugs, yet few drug regimens give high CR rates in patients with metastatic cancer, and cures for most types of metastatic cancer are very rare. Furthermore, the few types of cancers that are currently curable at a high rate with combination chemotherapy are generally characterized by properties that confer hypersensitivity to a particular chemotherapy drug or drugs. Extraordinary effort, resources and time have been expended without success to develop methods capable of high CR rates, and still over 580,000 people in the U.S. die of metastatic cancer each year. Presently, there are no methods for the effective treatment for most types of metastatic cancer that can give high CR rates or durable, long-term CRs in patients. Thus, a need exists to develop a cancer therapy that can achieve high rates of CRS, especially long-term durable CRs, in patients with metastatic cancer or refractory caner.

WO2014/066400 describes methods for the effective treatment of metastatic cancers that involve treatment with melphalan, BCNU, and redox cycling agents in conjunction with bone marrow stem cell infusion. The following reference relates to this matter and is hereby incorporated in its entirety by reference: WO2014/066400, Methods for the Effective Treatment of Metastatic Cancer.

In vitro, it is easy to profoundly decrease cellular GSH levels (and to consequently increase sensitivity to DNA-crosslinking drugs such as melphalan) by incubating cells with redox cycling agents or agents that generate reactive oxygen species. Many studies have demonstrated that ascorbic acid undergoes transition metal catalyzed autoxidation to produce hydrogen peroxide. In vitro, ascorbic acid and hydrogen peroxide can deplete GSH, induce oxidative stress, and kill cells. Riordan, in U.S. Pat. No. 5,639,787 (Therapeutic method for the treatment of cancer), teaches the use of high-dose intravenous ascorbic acid for the treatment of cancer. However, multiple clinical trials have failed to demonstrate anticancer activity of high-dose ascorbic acid in patients, and ascorbic acid has not provided a basis for obtaining high rates of complete responses in patients with metastatic cancer. The biologic activity of hydrogen peroxide is a function of the dose per cell or the dose per liter of intracellular fluid. Exposure of cells to ascorbic acid or hydrogen peroxide in vitro can result in doses per cell that are thousands of times higher than those that can be achieved in vivo. Hydrogen peroxide is rapidly decomposed in cells by glutathione peroxidase; in the process GSH is oxidized to GSSG. However, the GSSG in turn is reduced back to GSH by glutathione reductase with NADPH as the reductant. The reductive capacity of cells for GSSG far exceeds the flux of H2O2 that could be generated in vivo from even very high doses of ascorbic acid. This explains in part the absence of anticancer activity of ascorbic acid observed in multiple clinical trials. The following references relate to this matter and are hereby incorporated in their entirety by reference: Monti D A, et al., Phase I evaluation of intravenous ascorbic acid in combination with gemcitabine and erlotinib in patients with metastatic pancreatic cancer, PLoS One., 2012, 7(1); Wilson M K, et al., Review of high-dose intravenous vitamin C as an anticancer agent, Asia Pac J Clin Oncol., 2014 March, 10(1):22-37; Stephenson C M, et al., Phase I clinical trial to evaluate the safety, tolerability, and pharmacokinetics of high-dose intravenous ascorbic acid in patients with advanced cancer, Cancer Chemother Pharmacol. 2013 July, 72(1):139-46; Hoffer L J, et al., Phase I clinical trial of i.v. ascorbic acid in advanced malignancy, Ann Oncol., 2008 November, 19(11):1969-74; Welsh J L, et al., Pharmacological ascorbate with gemcitabine for the control of metastatic and node-positive pancreatic cancer (PACMAN): results from a phase I clinical trial, Cancer Chemother Pharmacol., 2013 March, 71(3):765-75.

The delivery of drugs into tumors is compromised by a number of factors including poor vascularization, increased interstitial fluid pressure, and increased flow of interstitial tumor fluid out of the tumor. Accordingly, the intravenous administration of redox cycling drugs to a patient will generally result in higher drug levels and greater biologic effect in normal tissues than in tumors. Therefore, the GSH depletion and resulting sensitization to melphalan by intravenously administered redox cycling agents will generally be greater in normal tissues than tumors.

In the presence of oxygen, hydroxocobalamin catalyzes the autoxidation of ascorbic acid. In vitro, the combination of hydroxocobalamin and ascorbic acid generates hydrogen peroxide, lowers GSH levels, and is cytotoxic. The process involves redox cycling of the cobalt between Co(III) and Co(II) oxidation states with ascorbate serving as the reductant and oxygen as the oxidant. The ascorbic acid is oxidized to the ascorbate free radical and ultimately dehydroascorbic acid (DHA). The following reference relate to this matter and are hereby incorporated in their entirety by reference: Akatov V S, et al., Combined vitamins B12b and C induce the glutathione depletion and the death of epidermoid human larynx carcinoma cells HEp-2, Biosci Rep., 2000 October, 20(5):411-7; Solovieva M E, et al., Vitamin B12b increases the cytotoxicity of short-time exposure to ascorbic acid, inducing oxidative burst and iron-dependent DNA damage, Eur J Pharmacol. 2007 Jul. 2, 566(1-3):206-14; Nazhat N B, et al., Destruction of vitamin B12 by reaction with ascorbate: The role of hydrogen peroxide and the oxidation state of cobalt, J. Inorg. Biochem., 1989 June, 36(2):75-81; Ahmad I, et al., Effect of ascorbic acid on the degradation of cyanocobalamin and hydroxocobalamin in aqueous solution: a kinetic study, AAPS PharmSciTech., 2014 October, 15(5):1324-33.

Each of ascorbic acid and hydroxocobalamin distributes in the extracellular fluid and is not preferentially taken up by tumor cells. Accordingly, one skilled in the art would expect that the combination of intravenous ascorbic acid and hydroxocobalamin would not selectively deplete GSH in tumor cells versus normal tissues. One skilled in the art would expect that the combination would equally sensitize normal tissues and tumor tissues to melphalan, and that any gain in tumor cell killing would be offset by increased toxicity to normal cells, which would limit the dose of melphalan that could be safely administered.

In animal models, the combination of DHA and hydroxocobalamin exerted potent anticancer effects, however the combination of ascorbic acid and hydroxocobalamin was ineffective. Initial reports of anticancer activity with hydroxocobalamin and ascorbic acid were corrected in a follow-on publication and attributed to the use of ascorbic acid that had already decomposed to DHA prior to administration. In mouse models of P388 lymphocytic leukemia, the combination of ascorbic acid and hydroxocobalamin had anticancer activity that was limited in extent and duration; survival was prolonged only by about 7 days. The following reference relates to this matter and is hereby incorporated in its entirety by reference: Poydock M E, Effect of combined ascorbic acid and B-12 on survival of mice with implanted Ehrlich carcinoma and L1210 leukemia, Am J Clin Nutr., 1991 December, 54(6 Suppl):1261S-1265S (see Appendix A). DHA is unstable in blood and decomposes intravascularly within seconds to 2,3-diketogulonic acid (2,3-DKG). The following references relate to this matter and are hereby incorporated in their entirety by reference: Pierson H F, et al., Depletion of extracellular cysteine with hydroxocobalamin and ascorbate in experimental murine cancer chemotherapy, Cancer Res. 1985 October, 45(10):4727-31; Poydock M E, Effect of combined ascorbic acid and B-12 on survival of mice with implanted Ehrlich carcinoma and L1210 leukemia, Am J Clin Nutr. 1991 December, 54(6 Suppl):1261S-1265S (see Appendix A); Poydock M E, et al., Mitogenic inhibition and effect on survival of mice bearing L1210 leukemia using a combination of dehydroascorbic acid and hydroxycobalamin, Am J Clin Oncol., 1985 June, 8(3):266-9; Koshiishi I, et al., Degradation of dehydroascorbate to 2,3-diketogulonate in blood circulation, Biochim Biophys Acta. 1998 Sep. 16, 1425(1):209-14.

Ascorbic acid alone has been proposed as a means to induce oxidative stress in tumors. The administration of high-dose ascorbic acid was shown to generate ascorbate free radical and hydrogen peroxide in the microdialysis fluid obtained from tumors and subcutaneous tissues. However, the levels of hydrogen peroxide measured in the microdialysis fluid reflect both hydrogen peroxide from the extracellular fluid and hydrogen peroxide generated in the microdialysis tubing. Hydrogen peroxide production in microdialysis tubing could be significant because the flow rate was slow, the ascorbic acid levels were high, and a 10,000 to 30,000 molecular weight serum factor catalyzes the autoxidation of ascorbic acid. This serum factor could be present in the microdialysis concentration at significant levels as the molecular weight cut-off of the dialysis membrane was 20,000. In addition, the levels of ascorbate free radicals detected in the microdialysate from subcutaneous extracellular fluid were significantly higher than those from tumor extracellular fluid. Since ascorbate free radicals undergo rapid disproportionation to DHA and ascorbic acid, this strongly suggests that the levels of DHA generated in subcutaneous extracellular fluid were higher than that generated in tumor extracellular fluid. The data indicate that ascorbic acid undergoes autoxidation in microdialysate from tumor extracellular fluid and extracellular fluid from normal tissue. It has been postulated, but not demonstrated, that the extracellular environment of tumors may contain higher levels of transition metals that can catalyze the autoxidation of ascorbic acid compared to normal tissues. Even if this is the case, the rate of autoxidation of ascorbic acid in tumors is slow. Mice given an intravenous infusion of hyperpolarized ascorbic acid demonstrated no detectable DHA in tumors. By contrast, after infusion of hyperpolarized DHA to mice, hyperpolarized ascorbic acid was readily detected in tumors. Furthermore, as already discussed, the rate of hydrogen peroxide production from the autoxidation of ascorbic acid is far less than the capacity of tissues to detoxify the hydrogen peroxide. The following references relate to this matter and are hereby incorporated in their entirety by reference: Chen Q, et al., Ascorbate in pharmacologic concentrations selectively generates ascorbate radical and hydrogen peroxide in extracellular fluid in vivo, Proc Natl Acad Sci U S A., 2007 May 22, 104(21):8749-54; Chen Q, et al., Pharmacologic doses of ascorbate act as a prooxidant and decrease growth of aggressive tumor xenografts in mice, Proc Natl Acad Sci U S A., 2008 Aug. 12, 105(32):11105-9; Chen Q, et al., Ascorbate in pharmacologic concentrations selectively generates ascorbate radical and hydrogen peroxide in extracellular fluid in vivo, Proc Natl Acad Sci U S A., 2007 May 22, 104(21):8749-54; Keshari K R, et al., Hyperpolarized 13C dehydroascorbate as an endogenous redox sensor for in vivo metabolic imaging, Proc Natl Acad Sci U S A., 2011 Nov. 15, 108(46):18606-11; Du J, et al., Ascorbic acid: chemistry, biology and the treatment of cancer, Biochim Biophys Acta., 2012 December, 1826(2):443-57.

Consider the consequences of adding a redox catalyst such as hydroxocobalamin at equal concentrations to the extracellular fluid of normal tissues and the extracellular fluid of tumors at a concentration that results in rapid ascorbic acid autoxidation (compared to the rate of autoxidation in tissues without the catalyst). The result would be essentially equal rates of ascorbic acid autoxidation in extracellular fluid from normal tissues and tumor tissues since the contribution of endogenous catalysts would be minor compared to the catalytic activity of the hydroxocobalamin. Accordingly, one skilled in the art would expect the administration of a catalyst such as hydroxocobalamin, which is taken up equally by tumors and normal tissues, would provide no basis for the selective depletion of GSH in tumors. One skilled in the art would expect that absent selective depletion of GSH in tumor cells, the toxicity of melphalan would be increased in both normal tissues and tumor cells, and that the increased toxicity to normal tissues would require a dose reduction to the patient, which would offset any gain in cytotoxicity to tumor cells by the GSH depleting agents. For example, L-buthionine-SR-sulfoximine (BSO) depletes GSH in both normal tissues and tumor tissues, and in patients BSO increases the toxicity of melphalan to normal bone marrow. Another example is misonidazole, which upon systemic administration depletes GSH non-selectively in both tumors and normal tissues. The combination of misonidazole and nitrogen mustard results in increased DNA crosslinking and increased toxicity to both normal tissues and tumor tissues, with the greatest toxicity increases seen in normal tissues. The enhancement of toxicity to both normal tissues and tumors by DNA-damaging drugs administered in combination with drugs that non-selectively inhibit DNA repair is a general occurrence. For example, it is seen with DNA-damaging agents in combination with O6-benzylguanine and poly (adenosine diphosphate [ADP]-ribose) polymerase (PARP) inhibitors. The following references relate to this matter and are hereby incorporated in their entirety by reference: Bailey H H, et al., Phase I clinical trial of intravenous L-buthionine sulfoximine and melphalan: an attempt at modulation of glutathione, J Clin Oncol., 1994 January, 12(1):194-205; Bailey H H, et al., Phase I study of continuous-infusion L-S, R-buthionine sulfoximine with intravenous melphalan, J Natl Cancer Inst., 1997 Dec. 3, 89(23):1789-96; Murray D, et al., Effect of misonidazole pretreatment on nitrogen mustard-induced DNA cross-linking in mouse tissues in vivo, Br J Cancer., 1984 December, 50(6):801-8; Friedman H S, et al., Phase I trial of carmustine plus O6-benzylguanine for patients with recurrent or progressive malignant glioma, J Clin Oncol., 2000 Oct. 15, 18(20):3522-8; Rajan A, et al., A phase I combination study of olaparib with cisplatin and gemcitabine in adults with solid tumors, Clin Cancer Res., 2012 Apr. 15, 18(8):2344-51.

As described herein, the unexpected result that the administration of ascorbic acid and hydroxocobalamin will result in selective delivery of hydrogen peroxide and DHA to tumors and the selective depletion of GSH in tumor cells has been discovered. Despite the fact that the delivery of ascorbic acid and hydroxocobalamin will be equal in tumor and normal tissues, the dose of DHA to tumor cells will be approximately 3 to 12 times greater than in most normal tissues, and the dose of hydrogen peroxide to tumor cells will be as much as 20 times greater. Surprisingly, the unexpected preferential delivery of DHA and hydrogen peroxide will result from increased interstitial fluid pressure, interstitial fluid, and poor vascularity, which are characteristic of tumors. This is unexpected because increased interstitial fluid pressure in tumors and poor tumor vascularity are well known barriers to tumor uptake of drugs. The following references relate to this matter and are hereby incorporated in their entirety by reference: Jang S H, et al., Drug delivery and transport to solid tumors, Pharm Res., 2003 September, 20(9):1337-50; Jain R K, Barriers to drug delivery in solid tumors, Sci Am., 1994 July, 271(1):58-65; Provenzano P P, et al., Hyaluronan, fluid pressure, and stromal resistance in pancreas cancer, Br J Cancer., 2013 Jan. 15, 108(1):1-8.

SUMMARY OF THE INVENTION

The present invention relates to effective methods of treating metastatic cancers to achieve high rates of complete responses (CRs) and especially long-term, durable CRs. The present invention includes a method for the treatment and effective treatment (as defined below) of metastatic cancers, where the method comprises the administration of a set of drugs comprising melphalan, BNCU, hydroxocobalamin, ascorbic acid, and optionally ethanol and bone marrow stem cell infusion. The present invention also relates to a method of sensitizing tumor cells to DNA-damaging agents, where the method comprises the administration of hydroxocobalamin and ascorbic acid in conjunction with an inhibitor of glutathione reductase. The invention also relates to a method of selectively delivering drugs to tumors, where the method comprises the systemic administration of two compounds, Agent 1 and Agent 2; wherein both compounds distribute into the extracellular space after systemic administration, and wherein Agent 1 and Agent 2 spontaneously react in the extracellular space to directly or indirectly generate one or more drugs referred to as Drug 1, Drug 2, . . . , Drug N; wherein said drugs exert the desired pharmacologic effect within the intracellular space and/or interstitial space; and wherein said drugs are rapidly degraded or detoxified in the intravascular space.

In a first aspect, the invention pertains to a method for the treatment of metastatic cancer or refractory metastatic cancer in a subject and comprises administering a combination of 1,3-bis(2-chloroethyl)-1-nitrosourea, melphalan, hydroxocobalamin, and ascorbic acid, or pharmaceutically acceptable salts of any of the foregoing, simultaneously or within a six-hour time period; wherein the melphalan dose is in the range of 20 to 200 mg/m2. In one embodiment, 1,3-bis(2-chloroethyl)-1-nitrosourea is administered at a dose range of 50 to 400 mg/m2; the melphalan is administered at a dose of 20 to 200 mg/m2; the hydroxocobalamin is administered at a dose of 25 to 20,000 mg/m2, and the ascorbic acid is administered at a dose of 1 gram to 150 grams. In another embodiment, the 1,3-bis(2-chloroethyl)-1-nitrosourea is administered at a dose range of 75 to 300 mg/m2; the melphalan is administered at a dose of 50 to 200 mg/m2; the hydroxocobalamin is administered at a dose of 400 to mg to 800 mg/m2, and the ascorbic acid is administered a dose of 5 grams to 40 grams. In a further embodiment, the 1,3-bis(2-chloroethyl)-1-nitrosourea is administered at a dose of 150 mg/m2; the melphalan is administered at a dose of 70-140 mg/m2; the hydroxocobalamin is administered at a dose of 580 mg/m2, and the ascorbic acid is administered a dose of 5 grams to 25 grams. In one embodiment, the invention further comprises the systemic administration of ethanol at a dose of 500 mg to 40 grams. In another embodiment, the invention further comprises bone marrow stem cell transplantation therapy. In a further embodiment, the metastatic cancer is in a subject with an inherited germline mutation in a gene involved in DNA repair, and/or homologous recombination, and/or DNA crosslink repair. In one embodiment, the metastatic cancer is in a patient with an inherited germline mutation in one or more of the following genes: ATR, BARD1, BLM, BRCA1, BRCA2, BRIP1 (FANCJ, BACH1), EME1, ERCC1, ERCC4, FAN1, FANCA, FANCB, FANCC, FANCD1, FANCD2, FANCE, FANCF, FANCG, FANCI, FANCJ, FANCL, FANCM, FANCN, FANCO, FANCP, FANCQ, FANCQ, FANCR, FANCS, FANCT, HELQ, MEN1, MUS81, NBN (NBS1), PALB2, RAD50, RAD51 (FANCR), RAD51C (FANCO), RAD51D, REV1, SLX4 (FANCP), UBE2T (FANCT), USP1, WDR48, XPF, XRCC2, XRCC3, or other genes involved in DNA-crosslink repair, homologous recombination, or DNA repair. In another embodiment, the metastatic cancer is in a subject with an inherited germline mutation in BRCA1 and/or BRCA2. In a further embodiment, the metastatic cancer is selected from pancreatic cancer, ovarian cancer, breast cancer, and prostate cancer.

In a second aspect, the invention pertains to a method for sensitizing cancer cells to DNA-damaging agents in vivo comprising the administration of a DNA-damaging agent, a glutathione reductase inhibitor, hydroxocobalamin, and ascorbic acid, or pharmaceutically acceptable salts of any of the foregoing.

In a third aspect, the invention pertains to a method of treating cancer comprising the administration of 1,3-bis(2-chloroethyl)-1-nitrosourea, hydroxocobalamin, and ascorbic acid, or pharmaceutically acceptable salts of any of the foregoing.

In a fourth aspect, the invention pertains to a method for the selective delivery of a drug to solid cancers for the treatment of cancer comprising:
a. Selecting two compounds referred to as Agent 1 and Agent 2; wherein Agent 1 and Agent 2 are not enzymes, and wherein said agents distribute into the extracellular space after systemic administration and spontaneously react to directly or indirectly generate one or more drugs; wherein said drugs are rapidly decomposed, degraded, or otherwise eliminated or detoxified from the intravascular compartment; wherein said drugs rapidly efflux from the interstitial fluid and enter the intracellular fluid; and wherein said drug(s) exert a cancer treatment effect.
b. Systemically administering Agent 1 and Agent 2.

In a fifth aspect, the invention pertains to a set of pharmaceutical compositions for use in effectively treating metastatic cancer or refractory metastatic cancer in a subject, comprising a therapeutically effective dose of 1,3-bis(2-chloroethyl)-1-nitrosourea, melphalan, hydroxocobalamin, and ascorbic acid, or pharmaceutically acceptable salts of any of the foregoing.

In a sixth aspect, the invention pertains to the use of a pharmaceutical compositions for the treatment of metastatic cancer or refractory metastatic cancer in a subject, comprising a therapeutically effective dose of a combination of 1,3-bis(2-chloroethyl)-1-nitrosourea, melphalan, hydroxocobalamin and ascorbic acid, wherein the melphalan dose is in the range of 20 to 200 mg/m2.

In a seventh aspect, the invention pertains to a method for the prevention of hemolysis and/or methemoglobin formation in a subjected treated with agents that generate hydrogen peroxide and comprises the systemic administration of a therapeutically effective dose of ethanol.

DETAILED DESCRIPTION OF THE INVENTION

The present invention relates to methods for the treatment and effective treatment (as defined below) of metastatic cancers, including refractory metastatic cancers.

A description of example embodiments of the invention follows.

Definitions

Acquired Drug Resistance: refers to the ability of populations of cancer cells to escape destruction or inactivation by a drug at levels that are clinically achievable, wherein said lack of sensitivity arises or evolves in an initially drug-sensitive population.

Analog: refers to a compound or moiety possessing significant structural similarity as to possess substantially the same function.

Allogeneic: refers to tissue or cells derived from another individual.

Appropriately selected patients: refers to patients who are good candidates for the treatment and that are likely to benefit. For example, a frail, elderly patient with serious underlying medical conditions (e.g., heart disease, liver disease, renal disease, severe malnutrition) would generally not be a good candidate. A patient with such advanced metastatic disease that he or she would be unlikely to survive the treatment would not be a good candidate. A patient with extensive metastatic disease to the brain would not be a good candidate. Methods for the appropriate selection of patients are well known to one skilled in the art.

Approximately: refers to plus or minus 25% when referring to drug doses and ranges of drug doses.

Area under the curve (AUC): refers to the integral of the drug concentration-time curve for a drug in vitro or in vivo; the AUC is a measure of total drug exposure.

Ascorbate free radical: refers to the radical formed from the one electron oxidation of ascorbic acid. The following reference relates to this matter and is hereby incorporated in its entirety by reference: Du J, et al., Ascorbic acid: chemistry, biology and the treatment of cancer, Biochim Biophys Acta., 2012 December, 1826(2):443-57.

Ascorbic acid: refers to L-ascorbic acid and the molecular species that are in equilibrium with ascorbic acid when ascorbic acid is dissolved in water or aqueous solutions. Ascorbic acid has two ionizable hydroxyl groups with pKa of 4.2 and pKa of 11.6, respectively. At physiological pH, the ascorbate monoanion is the predominant form, however, small amounts of the ascorbate dianion are also present; both are species are in equilibrium with ascorbic acid. Ascorbic acid also refers to pharmacologically acceptable salts of L-ascorbic acid, such as mono-sodium ascorbate. Ascorbic acid does not refer to DHA or ascorbate free radical. Doses of ascorbic acid are based on the content of L-ascorbic acid, assuming that all the drug were in the form of L-ascorbic acid. The following reference relates to this matter and is hereby incorporated in its entirety: Du J, et al., Ascorbic acid: chemistry, biology and the treatment of cancer, Biochim Biophys Acta, 2012 December, 1826(2):443-57.

AUC-:1 refers to the drug AUC needed to give a 1-log reduction in clonogenic cell survival.

Autologous: refers to tissue or cells derived from the same individual.

BCNU: refers to the drug carmustine, also known as 1,3-Bis(2-chloroethyl)-1-nitrosourea (CAS No. 154-93-8). BCNU inhibits glutathione reductase, which is critical to maintaining cellular GSH levels in the presence of oxidative stress. Glutathione reductase catalyzes the reduction by NADPH of GSSG to GSH. BCNU is also a DNA-cross-linking agent.

Bone marrow stem cell or hematopoietic stem cell: refers to a pluripotent cell that can reconstitute normal bone marrow and give rise to all normal bone marrow cell lineages; these cells are typically CD34+ cells, can be isolated from bone marrow aspirates, peripheral blood, and umbilical cord blood, and can be autologous or allogeneic. Cells that can give rise to bone marrow stem cells for the purposes of this application are also considered to be "bone marrow stem cells."

Bone marrow stem cell infusion, bone marrow stem cell transplantation therapy, and stem cell infusion: refer to the process of intravenously administering bone marrow stem cells to speed recovery of bone marrow function.

BRCA-associated cancer and BRCA-related cancer: refer to cancer that arises in the setting of an inherited BRCA mutation.

Buthionine sulfoximine (BSO): refers to a selective inhibitor of gamma-glutamylcysteine synthetase, the rate limiting enzyme in GSH synthesis.

Cancer: refers to a disease defined by malignant behavior. Only malignant cells (i.e., cells that engage in malignant behavior) can sustain the clinical disease of cancer.

Clonogenic survival: refers to the ability of a cell to multiply and form a colony of cells.

Clonogenic survival fraction: refers to a measure of clonogenic survival, calculated as the fraction of cells that are able to give rise to a colony of cells in a colony-forming assay, also equal to the probability of clonogenic survival.

Combination therapy: refers to the administration of therapeutic compounds (e.g., agents or drugs) in a manner wherein each therapeutic compound is administered at a different time, as well as to the administration of these therapeutic agents, or at least two of the therapeutic agents, concurrently or in a substantially simultaneous manner. Simultaneous administration can be accomplished, for example, by administering to the subject a single capsule having a fixed ratio of each therapeutic agent or by administering multiple, single capsules for each of the therapeutic agents, or substantially simultaneous administration of each therapeutic agent can be effected by any appropriate route, including oral routes, intravenous routes, intramuscular routes, or direct absorption through mucous membrane tissues. The therapeutic agents can be administered by the same route or by different routes. For example, a first therapeutic agent of the selected combination may be administered by intravenous injection while the other therapeutic agents of the combination may be administered orally. Alternatively, for example, all therapeutic agents may be administered orally or all therapeutic agents may be administered by intravenous injection. Therapeutic agents may also be administered in alternation. The combination therapies featured in the present invention can result in a synergistic effect in the treatment of a disease or cancer. Combination therapy also refers to the administration of the therapeutic agents as described above in further combination with other biologically active ingredients and non-drug therapies (e.g., surgery or radiation treatment). Where the combination therapy comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Complete Response (CR): refers to the absence of all detectable cancer, which is typically determined by CT scan, MRI or other imaging or detection technology; The following reference relates to this matter and is hereby incorporated in its entirety: Eisenhauer E A, et al., New response evaluation criteria in solid tumours: revised RECIST guideline (version 1.1), Eur J Cancer, 2009 January, 45(2):228-47. It should be noted that the RECIST guidelines equate the presence of tumor mass with the presence of cancer and decreases in tumor mass with anticancer efficacy. While tumor mass is an accurate metric for cytotoxic anticancer drugs and therapies that kill cancer cells, it is not an accurate metric for anticancer drugs that permanently abolish the potential for cell proliferation without necessarily killing cells. For example, bizelesin acts in this manner. By definition, cell populations (i.e., tumor masses) that do not and cannot proliferate, cannot exhibit malignant behavior and are not cancerous, even though said cell populations remain viable.

Current, established therapies: refers to existing regimens used to treat subjects.

Dehydroascorbic acid (DHA) refers to the oxidized form of ascorbic acid; (5R)-5-[(1S)-1,2-dihydroxyethyl]oxolane-2,3,4-trione.

Derivative: refers to a compound or moiety that has been further modified or functionalized from the corresponding compound or moiety.

Detoxification: refers to the process of decreasing or abolishing the cellular toxicity of a drug by means of spontaneous or cellular metabolic processes. For example, enzymatic or spontaneous nucleophilic reaction of GSH with an alkylating agent results in detoxification of the alkylating agent.

2,3-Diketogulonic acid: refers to (4R,5S)-4,5,6-trihydroxy-2,3-dioxohexanoic acid, which is a decomposition product of DHA, (CAS No. 3409-57-2).

Distribute into the extracellular fluid: means that the volume of distribution of the drug is essentially the extracellular fluid space in the body.

DNA interstrand crosslinking agent: refers to a drug or chemical agent that binds the DNA strands of the DNA double helix together with sufficient affinity as to preclude strand separation and thereby impairs DNA synthesis. In general, but not always, said binding affinity results from covalent bonds formed between the crosslinking agent and the DNA strands. Examples of DNA-crosslinking agents are provided in the following, which is hereby incorporated by reference in its entirety: Raj ski S R, et al., DNA Cross-Linking Agents as Antitumor Drugs., Chem Rev., 1998 Dec. 17, 98(8):2723-2796.

Dose modification factor: refers to the following formula: [drug concentration that gives a 1-log reduction in clonogenic cell survival without the second drug(s) "X"]/[drug concentration that gives a 1-log reduction with drug(s) "X"]. For example, the drug could be melphalan and drug "X" could be BSO.

Durable complete response (also long-term CR): refers to a long-lasting CR; or a CR lasting at least 1 year off chemotherapy; or a CR lasting for a period of time greater than 0.5 X, wherein X is the median overall survival of comparable patients with the same type and stage of cancer who are treated with current, established therapies and fail to have a CR. For example, if the median overall survival for a particular type and stage of cancer were 18 months with current, established therapies in patients that failed to have a CR, then for a CR to be considered a durable CR in this setting, it would have to exceed 9 months in duration.

Effective treatment of metastatic cancer or effectively treating cancer: refers to a treatment or method that in appropriately selected patients gives high rates or high probabilities of one or more of the following: CRs, durable long-term CRs; long-term progression-free survival, long-term overall survival, long-term disease-specific survival, long-term relative survival, long-term disease-free survival, and apparent cures; and which generally preserves or improves the patient's quality of life. A grant of breakthrough therapy designation by the Food and Drug Administration (FDA) would provide supportive evidence of effectiveness; however, a treatment that is statistically superior to placebo, prolonged overall survival or progression free survival by several months and received FDA approval would by our definition not be deemed an effective treatment. Similarly, a treatment that gives high rates (e.g., 80%) of short-term (e.g., several months duration) CRs would not be deemed an effective treatment.

Electrophilic DNA-crosslinking agent: refers to a DNA-crosslinking agent that reacts with nucleophilic sites on DNA; for example, the bifunctional alkylating agent melphalan is an electrophilic DNA-crosslinking agent that reacts with two nucleophilic centers on DNA: N-7 of guanine and N-3 of adenine.

Enzyme: refers to a protein that catalyzes a chemical reaction.

Extracellular fluid: refers to the fluid that resides outside of cells in the body; the corresponding space is referred to the extracellular space. For purposes of this application, extracellular fluid can be viewed as the plasma and interstitial fluid.

Fanconi/BRCA pathways of DNA repair: refers to the cellular machinery, proteins, and processes involved in homologous recombination and the repair of DNA interstrand crosslinks. The following references relates to this matter and are hereby incorporated by reference in its entirety: Kim H, et al., Regulation of DNA cross-link repair by the Fanconi anemia/BRCA pathway, Genes Dev., 2012 Jul. 1, 26(13):1393-408; Moldovan GL, How the Fanconi anemia pathway guards the genome, Annu Rev Genet., 2009, 43:223-49.

Glutathione (GSH): refers to a tripeptide with a gamma peptide bond between the amine group of cysteine and the carboxyl group of the glutamate side-chain, where the cysteine is attached by peptide bond to glycine. GSH is the major intracellular thiol compound: it is an important antioxidant and an important agent in the intracellular detoxification of reactive electrophiles, such as alkylating agents.

Glutathione peroxidase: refers to an enzyme that catalyzes the conversion of hydrogen peroxide into water and GSH into GSSG.

Glutathione reductase (GR): refers to an enzyme that catalyzes the reduction of GSSG into GSH; NADPH is used as the reducing agent.

Glutathione disulfide (GSSG): refers to the compound formed by linking two GSH molecules by a disulfide bond; also, referred to as "oxidized GSH."

Glutathionylation: refers to the formation of mixed disulfides between glutathione and low-pKa cysteinyl residues of proteins. The following reference relates to this matter and is hereby incorporated by reference in its entirety: Dalle-Donne I, et al., S-glutathionylation in protein redox regulation, Free Radic Biol Med., 2007 Sep. 15, 43(6):883-98.

High rate (or probability) of complete responses: refers to a rate (or probability) of CR that is at least approximately two times the rate (or probability) obtained with current, established treatments for the particular type and stage of cancer, wherein the term "the particular type" of cancer can refer not only to the histological type (i.e., serous ovarian cancer), but also to other clinically relevant qualifying properties such as platinum-resistance; or, alternatively, a rate exceeding approximately 50%. The term "high probability of complete response" is preferred when dealing with a single patient, but otherwise the terms "high rate" and "high probability" are essentially interchangeable.

Homologous recombination: refers to a DNA repair process that results in the removal and repair of DNA interstrand crosslinks and the repair of DNA double stranded breaks. The following references relates to this matter and are hereby incorporated by reference in its entirety: Kim H, et al., Regulation of DNA cross-link repair by the Fanconi anemia/BRCA pathway, Genes Dev., 2012 Jul. 1, 26(13):1393-408; Moldovan GL, How the Fanconi anemia pathway guards the genome, Annu Rev Genet., 2009, 43:223-49.

Includes (as well as including and other forms of the word): shall be construed as includes (or including, etc.) without limitation or "includes but is not limited to."

Inhibitor of glutathione reductase: refers to a drug or agent that inhibits GR activity or that spontaneously or after metabolic activation generates a chemical species that inhibits GR activity.

Interstitial fluid or interstitial water: refers to extravascular fluid that is located outside of cells.

Interstitial space: refers to the space occupied by interstitial fluid.

Intracellular water or fluid: refers to water or fluid that is located inside cells.

Intracellular GSSG/2GSH reduction potential: refers to a metric that provides a measure of the reducing activity of GSH under the intracellular conditions; it is given by $\Delta E$ in the Nernst equation: $\Delta E = E_{ph} - RT/2F \ln [GSH]^2/[GSSG]$, wherein $E_{ph}$ is $E_0$ (the reduction potential under standard state conditions) adjusted to the intracellular pH; R is the gas constant, F is the Faraday constant, T is the temperature, [GSH] is the glutathione concentration, and [GSSG] is the glutathione disulfide concentration at the intracellular location. At pH 7.0 $E_{ph} = \sim -240$ mV, and at 37° C., $\Delta E = \sim -240 - 30.8 \log [GSH]^2/[GSSG]$ in mV. The following reference which relates to this matter is hereby incorporated by reference in its entirety: Schafer F Q, et al., Redox environment of the cell as viewed through the redox state of the glutathione disulfide/glutathione couple, Free Radic Biol Med., 2001 Jun. 1, 30(11):1191-212.

Interstitial fluid pressure: refers to the pressure exerted by interstitial fluid. The following reference relates to this matter and is hereby incorporated in its entirety by reference: Guyton A C, A concept of negative interstitial pressure based on pressures in implanted perforated capsules, Circ Res., 1963 April, 12:399-414.

Intrinsic drug resistance: refers to the ability of populations of cancer cells to escape destruction or inactivation by a drug at levels that are clinically achievable, wherein said lack of sensitivity is manifest prior to drug exposure.

Irreversible inhibitor: refers to an agent that permanently inactivates an enzyme; generally, this occurs by covalent modification of the enzyme at site(s) that are essential for enzyme activity.

Liquid cancer: refers to a cancer derived from the bone marrow or lymphatic tissues; examples include leukemia, lymphoma, and myeloma.

Log reduction in cell survival: is the negative logarithm of the fraction of clonogenic cancer cells that survive the treatment; that is, each log reduction reduces the number of surviving clonogenic cancer cells by nine tenths. For example, a 1-log reduction means that the treatment results in a 90% decrease in clonogenic cell survival, a 2-log reduction corresponds to a 99% decrease in clonogenic cell survival, a 3-log reduction corresponds to a 99.9% decrease in clonogenic cell survival, etc.

Malignant behavior: refers to proliferation and invasiveness in an abnormal context or setting in the body, wherein invasiveness is the expansion of cells into new space, which can be local or distant (i.e., metastatic), with the remodeling or destruction of existing tissue architecture and the creation of infrastructure to support the metabolic needs of the cells; the mechanisms of invasiveness can be carried out by malignant cells and/or non-malignant cells in the microenvironment. Malignant behavior is the defining property of cancer.

Malignant cell: refers to a cancer cell that expresses or can express malignant behavior; not all tumor cells in a patient with cancer are malignant; many tumor cells in patients with cancer are dead-end, cannot proliferate, cannot engage in malignant behavior, and are not malignant cells.

Melphalan (CAS No. 148-82-3): is a bifunctional alkylating agent that crosslinks DNA and thereby inhibits cancer cell clonogenic survival.

Metastatic cancer: refers to cancer that has spread beyond the local tissue site of origin to distant locations in the body; that is, non-localized cancer. Micro-metastatic cancer is metastatic cancer that is not detectable with conventional imaging technology because of the small size of the metastatic lesions.

mg/m2 and gram/m2: refer to the dose per square meter of body surface area. Methods for calculating body surface area are well known to one skilled in the art. Doses expressed in mg/m2 or grams/m2 can be converted into approximately equivalent or similar doses based on body weight or other metrics well known to one skilled in the art; embodiments of the present invention in which doses are expressed in mg/kg or other such metrics are within the scope of the present invention.

NADPH: refers to the reduced form of nicotinamide adenine dinucleotide phosphate (NADP).

Nitrogen mustard analog: refers to a compound containing two or more chloroethylamine groups or an analog thereof; a compound that can transform in vivo or vitro into one with chloroethylamine groups; or a compound that can form aziridinyl groups. Chloroethylamine undergoes intramolecular nucleophilic reactions with elimination of Cl— and forms aziridinyl groups.

Neoadjuvant setting: refers to the administration of a chemotherapeutic drug or therapy before surgical resection of the primary tumor.

Non-homologous end joining (NHEJ): refers to a process for the repair of double stranded DNA breaks that results in error-prone repair. The following reference which relates to this matter is hereby incorporated by reference in its entirety: Mladenov E, et al., Induction and repair of DNA double strand breaks: the increasing spectrum of non-homologous end joining pathways, Mutat Res., 2011 Jun. 3, 711(1-2):61-72.

Non-refractory metastatic cancer: refers to metastatic cancer of a type that can be effectively treated with current, established therapies; examples include most but not all testicular cancers, childhood acute lymphocytic leukemia, Hodgkins lymphoma, follicular thyroid cancer, and other cancers that are well known to one skilled in the art.

Nucleotide excision repair (NER): refers to a DNA repair process that removes nucleotides with bulky modifications and repairs the damage. The following reference which relates to this matter is hereby incorporated by reference in its entirety: Kamileri I, et al., Nucleotide excision repair: new tricks with old bricks, Trends Genet., 2012 November, 28(11):566-73.

Oxidative stress: refers to the condition that exists when the levels of reactive oxygen species exceed the ability of cells to maintain those reactive chemical species within normal, physiological or acceptable levels; oxidative stress is generally associated with an increase the intracellular GSSG/2GSH reduction potential and oxidative damage to biomolecules. The following reference relates to this matter and is hereby incorporated in its entirety: Karihtala P, et al., Reactive oxygen species and antioxidant mechanisms in human tissues and their relation to malignancies, APMIS., 2007 February, 115(2):81-103. Some methods for measuring oxidative stress are reviewed in: Halliwell B, et al., Measuring reactive species and oxidative damage in vivo and in cell culture: how should you do it and what do the results mean? Br J Pharmacol., 2004 May, 142(2):231-55.

Pharmacologic effect: refers to an action imparted by a drug on a subject or on cells in the subject; for example, a decrease in cellular GSH, or cytotoxicity are pharmacologic effects.

Potential for cell proliferation: refers to the ability of cells to proliferate; or clonogenic survival as measured by the ability to form colonies of cells. The potential for cell proliferation differs from cell proliferation: all malignant cells by definition have the potential for cell proliferation all the time, but most malignant cells are not actively engaged in proliferation most of the time, as cell proliferation is episodic.

Probability of clonogenic survival: refers to clonogenic survival fraction.

Prodrug refers: to a derivative of a drug that can be transformed in vivo or in vitro either spontaneously or as a result of metabolism or enzyme activity into the parent drug.

Reactive oxygen species (ROS): refer to reactive oxygen-related species such as superoxide ($O_2$-), hydrogen peroxide ($H_2O_2$), hydroxy radical (OH•), peroxy radicals (ROO•), nitric oxide (NO•), and peroxynitrite anion (ONOO—). The following reference relates to this matter and is hereby incorporated in its entirety: Valko M, et al., Free radicals, metals and antioxidants in oxidative stress-induced cancer; Chem Biol Interact., 2006 Mar. 10, 160(1):1-40.

Redox cycling: refers to a series of chemical reactions in which a compound is reduced and the product is then oxidized by reaction with molecular oxygen; the catalytic cycle can repeat many times and consume large quantities of the reducing agent and large quantities of oxygen. For example, quinones can be reduced by a variety of cellular enzymes by one electron transfer from NADH or NADPH to give semi-quinone radicals, which can react with oxygen to regenerate the quinone and give superoxide. Redox cycling causes oxidative stress in cells by generating large amounts of superoxide and other reactive oxygen species. Redox cycling can be represented as repetitive cycles of equations 1 and 2: Equation 1: $E+R \rightarrow R—*+E+$ Equation 2: $R—*+O_2 \rightarrow R+O_2-$; where E is an electron donor, E+ is the oxidized form of E, and R—* is a free radical.

Redox cycling agent (or drug): refers to a compound that engages in redox cycling; the term can refer to the reduced and/or oxidized form of the cycling chemical species that repetitively undergoes changes in oxidation/reduction status; it is also used to refer to compounds that can generate by spontaneous or metabolic processes a redox cycling agent.

Refractory metastatic cancer: refers to metastatic cancer that has failed to adequately respond to therapy; or metastatic cancer of a type that is known to be generally unresponsive to existing therapies and that cannot be effectively treated with current, established therapies. For example, metastatic testicular cancer is highly curable and is generally not a refractory metastatic cancer; by contrast, pancreatic cancer, melanoma, and platinum-resistant ovarian cancers are refractory metastatic cancers. A patient need not have failed on treatment to be considered to have refractory metastatic cancer. A cancer is considered refractory to a particular drug if the type of cancer is known not to respond well to the particular drug. For example, pancreatic cancer is refractory to BCNU, melphalan, and high-dose ascorbic acid. The following references relate to this matter and are hereby incorporated by reference in their entirety: Kovach J S, et al., Proceedings: A controlled study of combined 1,3-bis-(2-chloroethyl)-1-nitrosourea and 5-fluorouracil therapy for advanced gastric and pancreatic cancer, Cancer., 1974 February, 33(2):563-7; Smith D B, et al., Phase II evaluation of melphalan in adenocarcinoma of the pancreas, Cancer Treat Rep., 1985 July-August, 69(7-8):917-8; Monti D A, et al., Phase I evaluation of intravenous ascorbic acid in combination with gemcitabine and erlotinib in patients with metastatic pancreatic cancer, PLoS One, 2012, 7(1).

Sensitize cancer cells to a DNA-crosslinking agent or DNA-damaging agent: means to increase the sensitivity of cancer cells to the agent, which results in said agent causing a much greater inhibition of cancer clonogenic survival with a decrease in the AUC or dose of the agent needed to give a 1-log reduction in cancer cell clonogenic survival by a factor of at least 3; the degree of sensitization is measured by the dose modification factor (DMF).

Set of drugs (e.g., agents or compositions) for use in a regimen to treat (a specified condition): refers to one or more drugs; if the set comprises drug #1, drug #2, drug #3 and drug #4, then the term "a set of drugs for use in a regimen to treat (a specified disease) means:
drug #1 for use in a regimen to treat (a specified disease),
drug #2 for use in a regimen to treat (a specified disease),
drug #3 for use in a regimen to treat (a specified disease),
and drug #4 for use in a regimen to treat (a specified disease), wherein the regimen involves the combined use of drug #1, drug #2, drug #3, and drug #4. Set of drugs also refers to a kit comprising said drugs.

Solid cancers or solid tumors: refers to a cancer derived from a solid tissue; examples include pancreatic cancer, colon cancer, lung cancer, and ovarian cancer.

Subject: refers to a mammal in need of treatment or prevention, e.g., humans, companion animals (e.g., dogs, cats, and the like), farm animals (e.g., cows, pigs, horses, sheep, goats, and the like), and laboratory animals (e.g., rats, mice, guinea pigs, and the like). Typically, the subject is a human in need of the specified treatment.

Selective delivery of drugs to a tumor: refers to the systemic administration of one or more agents to a subject and achieving drug levels in tumors and/or the intracellular fluid of tumor cells that are greater than the levels in normal tissue, wherein the magnitude of the increased delivery of the drug to tumors is sufficient to preferentially elicit a desired pharmacologic effect of said drug in tumors.

Selective (effect) in tumors (or tumor cells): refers to achieving a magnitude of an effect in tumors (or tumor cells) that is greater than the magnitude in normal tissue, wherein the magnitude of the increased effect in tumors (or tumor cells) is sufficient to preferentially elicit a desired pharmacologic effect in the tumors (or tumor cells).

Synergy or synergistic effect: refers to a detectable effect that is greater (i.e., in a statistically significant manner relative to an appropriate control condition) in magnitude than the sum of the effects that can be detected when the compounds are used alone: that is, the effect of the combination is greater than the expected additive effect of each component. A synergistic effect may be an effect that cannot be achieved by administration of any of the compounds or other therapeutic agents as single agents. A synergistic effect may include an effect of treating cancer by reducing tumor size, inhibiting tumor growth, or increasing survival of the subject. A synergistic effect may also include reducing cancer cell viability, inducing cancer cell death, or inhibiting or delaying cancer cell growth.

Systemic administration: refers to the administration of a drug the results in drug distribution in the body by means of the blood circulation; it includes intravenous (IV), intra-arterial, intraperitoneal, and oral routes of drug administration. A preferred route is IV.

Therapeutically effective dose: refers to a dose that gives the beneficial treatment effect.

Thiolate: the negatively charged conjugate base of a thiol; a deprotonated thiol ion. In cells, the protein thiolate content is largely determined by the content of cysteine thiol groups that have a pKa of approximately 7 or less.

Treatment: refers to a therapy that provides a beneficial effect to a patient with a respect to a disease or condition.

USP: refers to The U.S. Pharmacopeial Convention (USP) drug standards.

Equivalents

Those skilled in the art can recognize or be able to ascertain, using no more than routine experimentation, many equivalents to the inventions, materials, methods, and components described herein. Such equivalents are intended to be within the scope of the claims of this patent. While this invention has been particularly shown, and described with references to preferred embodiments thereof, it will be understood by those skilled in the art that various changes in form and details may be made therein without departing from the scope of the present invention.

Embodiment E1

Embodiment E1 is a method for the selective delivery of drugs to solid cancers and for achieving pharmacological effect(s) for the treatment of cancer. The method comprises:
a. Selecting two compounds referred to as Agent 1 and Agent 2; wherein said agents are not enzymes, and wherein said agents distribute into the extracellular space after systemic administration, wherein Agent 1 and Agent 2 spontaneously react in the extracellular space to directly or indirectly generate one or more drugs referred to as Drug 1, Drug 2, . . . Drug N; wherein said drug(s) are rapidly decomposed, degraded, or otherwise eliminated or detoxified from the intravascular compartment; wherein said drug(s) rapidly efflux from the interstitial fluid and enter the intracellular fluid; and wherein said drug(s) exert the pharmacologic effect(s) and treatment effects.
b. Systemically administering Agent 1 and Agent 2 at doses sufficient to achieve the desired pharmacologic effect and treatment in the tumor.
c. Optionally administering ethanol
d. Optionally administering a glutathione reductase inhibitor(s)
e. Optionally administering a DNA-damaging agent(s)
f. Optionally administering bone marrow stem cells

Embodiment Ee1

Embodiment Ee1 of the present invention is a set of drugs for use in a treatment regimen for the selective delivery of drugs to solid cancers to achieve pharmacological effect(s) for the treatment of cancer, wherein the set of drugs comprises Agent 1 and Agent 2; wherein said agents are not enzymes, and wherein:

a. said agents distribute into the extracellular space after systemic administration, wherein Agent 1 and Agent 2 spontaneously react in the extracellular space to directly or indirectly generate one or more drugs referred to as Drug 1, Drug 2, . . . Drug N; wherein said drug(s) are rapidly decomposed, degraded, or otherwise eliminated or detoxified from the intravascular compartment; wherein said drug(s) rapidly efflux from the interstitial fluid and enter the intracellular fluid; and wherein said drug(s) exert the desired pharmacologic effect(s) and treatment effect; and wherein
b. the regimen involves the systemic administration of sufficient doses of Agent 1 and Agent 2 to obtain the pharmacologic and treatment effects in the tumor; and wherein
c. The regimen optionally involves administering ethanol; and wherein
d. The regimen optionally involves administering a glutathione reductase inhibitor; and wherein
e. The regimen optionally involves administering a DNA-damaging agent(s); and wherein
f. The regimen optionally involves administering bone marrow stem cells.

In E1 and Ee1, the term "rapidly" means that the rate of Drug 1 elimination or uptake is at least two times faster than the rate of production of Drug 1. The term "react in the extracellular space to directly or indirectly generate one or more drugs" means that in the presence of Agent 1 and Agent 2, the drug(s) are formed.

Embodiments E1 and Ee1 apply to the types of cancers given in LIST A, excluding the liquid cancers (e.g., excluding leukemias).

Pharmacologic Effects

In E1 and Ee1, the pharmacologic effects include one or more of the following: selective induction of oxidative stress in tumors, selective depletion of glutathione in tumors, selective increase in the intracellular GSSG/2GSH reduction potential in tumors, selective inhibition of tumor cell ATP production, selective inhibition of glycolysis in tumor cells, selective sensitization of tumor cells to DNA-damaging agents, selective sensitization of tumor cells to DNA-cross-linking agents, selective inhibition of tumor cell growth, and selective cytotoxicity to tumor cells.

Mode of Administration

In a preferred embodiment, the route of administration is intravascular, and a preferred route is intravenous (IV). Agent 1 and Agent 2 can also be given intra-arterially, intraperitoneally or orally. Prodrugs of Agent 1 and Agent 2 can also be employed and are within the scope of the present invention.

Agent 1 as a Redox Cycling Catalyst

In preferred embodiments of E1 and Ee1, Agent 1 undergoes redox cycling in the presence of Agent 2 and oxygen. In this cyclic process, Agent 1 is reduced by Agent 2, and the reduced form of Agent 1 is then oxidized by electron transfer to oxygen. The net result is that Agent 1 serves as a catalyst for the oxidation of Agent 2, and hydrogen peroxide is directly or indirectly produced. A large number of redox cycling catalysts that can be employed as Agent 1 are known to those skilled in the art.

The following reference relates to this matter and is hereby incorporated in their entirety by reference: Vlasova E A, et al., Kinetics and mechanism of the Co(II)-assisted oxidation of L-ascorbic acid by dioxygen and nitrite in aqueous solution, Dalton Trans., 2009 Dec. 21, (47):10541-9.

Hydroxocobalamin as the Redox Cycling Catalyst, Agent

In a preferred embodiment, Agent 1 is hydroxocobalamin. The Co(III) atom of hydroxocobalamin cycles between Co(III) and Co(II) states in the presence of a reducing agent and oxygen. A large number of hydroxocobalamin analogs in which the cobalt atom or another transition metal atom can undergo redox cycling are known to one skilled in the art. These are within the scope of the present invention. Examples of analogs, derivatives, prodrugs, and pharmacologically acceptable salts of hydroxocobalamin include hydroxocobalamin acetate (CAS #22465-48-1), hydroxocobalamin hydrochloride, vitamin B12r, diaquacob(III)inamide (CAS #15259-55-9); methylaquacobinamide (CAS #15653-35-7), adenosylaquacob(III)inamide (CAS #89302-86-3), and cyanoaquacob(III)inamide (CAS #13963-62-7). The following references relate to this matter and are hereby incorporated in their entirety by reference: Solovieva M E, et al., Vitamin B12b enhances the cytotoxicity of dithiothreitol, Free Radic Biol Med., 2008 May 15, 44(10):1846-56; Hackman, RA, Electron transfer reactions of macrocyclic compounds of cobalt, 1978, Thesis Submitted to Iowa State University; Jacobsen, D W, et al., Catalysis of thiol oxidation by cobalamins and cobinamides: reaction products and kinetics, Biochemistry, 1984, 23(9):2017-25.

Agent 2 as a Reducing Agent

In preferred embodiments of E1 and Ee1, Agent 2 is a reducing agent that can reduce Agent 1. More than one reducing agent can also be used at the same time. If Agent 1 is hydroxocobalamin, the reducing agent can be ascorbic acid, D-ascorbic acid (CAS No. 89-65-6), or a racemic mixture of D and L ascorbic acid; or a thiol such as cysteine, n-acetyl cysteine, glutathione, sodium 2-sulfanylethane-sulfonate (Mesna), or 6,8-dimercaptooctanoic acid (dihydrolipoic acid), or pharmacologically acceptable salts or prodrugs thereof. A wide range of other compounds can undergo autoxidation in the presence of hydroxocobalamin with the production of hydrogen peroxide. One skilled in the art will recognize other compounds that would behave in a similar fashion; these are within the scope of the present invention. Methods for the systemic administration of thiols are well known to one skilled in the art.

Agent 2 as Ascorbic Acid

In a preferred embodiment, Agent 2 is ascorbic acid, or a prodrug, derivative or analog thereof. A large number of pharmacologically acceptable salts, prodrugs, derivatives and analogs of ascorbic acid that can function as reducing agents are well known to one skilled in the art and are within the scope of the present invention.

DHA as Drug 1 and Hydrogen Peroxide as Drug 2

In a preferred embodiment, Agent 1 and Agent 2 react to generate hydrogen peroxide, ascorbate free radical and/or dehydroascorbic acid (DHA) and 2,3-diketogulonic acid (2,3-DKG). Ascorbate free radicals undergo rapid dismutation to ascorbic acid and DHA. The hydrogen peroxide may be generated directly or indirectly, for example by dismutation of superoxide. Hydrogen peroxide, DHA and 2,3-DKG can mediate useful selective pharmacologic effects in cancer cells including: depletion of GSH, increase in the intracellular GSSG/2GSH reduction potential, inhibition of tumor cell ATP production, inhibition of glycolysis, the sensitization of tumor cells to DNA-damaging agents, sensitization of tumor cells to DNA-crosslinking agents, inhibition of mitosis, and cytotoxicity.

Hydroxocobalmin and Ascorbic Acid

In preferred embodiments of E1 and Ee1, Agent 1 is hydroxocobalamin, Agent 2 is ascorbic acid, Drug 1 is hydrogen peroxide, and Drug 2 is DHA. 2,3-DKG also results from the degradation of DHA and can exert useful pharmacologically effects. Derivatives, analogs or prodrugs of hydroxocobalamin and ascorbic acid can also be used and are within the scope of the present invention.

Reaction of Hydroxocobalmin and Ascorbic Acid

Hydroxocobalamin acts a catalyst for the oxidation of ascorbic acid. Hydroxocobalamin undergoes redox cycling in the presence of ascorbic acid and oxygen. In this cyclic process, hydroxocobalamin is reduced by ascorbic acid, and the reduced form of hydroxocobalamin is then oxidized by electron transfer to oxygen. The net result is that hydroxocobalamin serves as a catalyst for the oxidation of ascorbic acid, and hydrogen peroxide and DHA are produced. In vitro, the combination of hydroxocobalamin and ascorbic acid generates hydrogen peroxide, lowers GSH levels, and is cytotoxic. The following references relate to this matter and are hereby incorporated in their entirety by reference: Akatov V S, et al., Combined vitamins B12b and C induce the glutathione depletion and the death of epidermoid human larynx carcinoma cells HEp-2, Biosci Rep., 2000 October, 20(5):411-7; Solovieva M E, et al., Vitamin B12b increases the cytotoxicity of short-time exposure to ascorbic acid, inducing oxidative burst and iron-dependent DNA damage, Eur J Pharmacol., 2007 Jul. 2, 566(1-3):206-14; Nazhat N B, et al., Destruction of vitamin B12 by reaction with ascorbate: The role of hydrogen peroxide and the oxidation state of cobalt, J. Inorg. Biochem., 1989 June, 36(2):75-81; Ahmad I, et al., Effect of ascorbic acid on the degradation of cyanocobalamin and hydroxocobalamin in aqueous solution: a kinetic study, AAPS PharmSciTech., 2014 October, 15(5):1324-33.

Hydroxocobalmin Dose and Timing

The dose of hydroxocobalamin in preferred embodiments of E1 and Ee1 is in the range of approximately 50 to 40,000 mg of hydroxocobalamin. In preferred embodiments, the hydroxocobalamin dose is for approximately 50 mg, 100 mg, 250 mg, 500 mg, and 1, 2, 3, 4, 5, 6, 7, 8, 9, 10, 11, 12, 13, 14, 15, 16, 17, 18, 19, 20, 25, 30, 35, and 40 grams. Methods for the intravenous administration of hydroxocobalamin are well known to one skilled in the art. Both the hydroxocobalamin and ascorbic acid can be given simultaneously or essentially at the same time. Alternatively, the hydroxocobalamin can be given hours prior to the ascorbic acid because hydroxocobalamin has a plasma half-life of approximately 26 to 31 hours. In preferred embodiments, the hydroxocobalamin is given over approximately 1, 2, 5, 10, 15, 20, 25, 30, 45, and 60 minutes. In a preferred embodiment, the hydroxocobalamin is given over approximately 10-15 minutes immediately prior to the administration of the ascorbic acid, which is given over a time period of approximately 30-60 minutes. Hydroxocobalamin is currently used intravenously for the treatment of cyanide poisoning. The following reference relates to this matter and is hereby incorporated in its entirety by reference: Prescribing information for Cyanokit.

Ascorbic Acid Dose and Administration

The dose of ascorbic acid in preferred embodiments of E1 and Ee1 is in the range of approximately 0.5 grams to 150 grams. In preferred embodiments of E1 and Ee1, the dose of ascorbic acid is approximately 0.5, 1, 2, 5, 10, 15, 20, 25, 30, 35, 40, 50, 60, 70, 80, 90, 100, 125, and 150 grams. Methods for the intravenous administration of ascorbic acid are well known to one skilled in the art. The ascorbic acid is given intravenously over approximately 5-360 minutes. In preferred embodiments, the ascorbic acid is given over approximately 5, 10, 15, 20, 25, 30, 35, 40, 45, 50, 55, 60, 70, 80, 90, 100, 120, 140, 160, 180, and 360 minutes. Intravenous ascorbic acid has been used in multiple clinical trials. The following references relate to this matter and are hereby incorporated in their entirety by reference: Monti D A, et al., Phase I evaluation of intravenous ascorbic acid in combination with gemcitabine and erlotinib in patients with metastatic pancreatic cancer, PLoS One., 2012, 7(1); Wilson M K, et al., Review of high-dose intravenous vitamin C as an anticancer agent, Asia Pac J Clin Oncol., 2014 March, 10(1):22-37; Stephenson C M, et al., Phase I clinical trial to evaluate the safety, tolerability, and pharmacokinetics of high-dose intravenous ascorbic acid in patients with advanced cancer, Cancer Chemother Pharmacol., 2013 July, 72(1):139-46; Hoffer L J, et al., Phase I clinical trial of i.v. ascorbic acid in advanced malignancy, Ann Oncol., 2008 November, 19(11):1969-74; Welsh J L, et al., Pharmacological ascorbate with gemcitabine for the control of metastatic and node-positive pancreatic cancer (PACMAN): results from a phase I clinical trial, Cancer Chemother Pharmacol., 2013 March, 71(3):765-75.

Pharmacologic Effects

Both hydroxocobalamin and ascorbic acid rapidly distribute into the extracellular fluid compartment following systemic administration. In the presence of oxygen, hydroxocobalamin and ascorbic acid react to generate hydrogen peroxide and DHA. Hydrogen peroxide and DHA are both rapidly cleared from the intravascular compartment and rapidly efflux the interstitial fluid and enter the intracellular fluid. Pharmacologic effects of DHA and hydrogen peroxide include the selective induction of oxidative stress in tumors, the selective depletion of glutathione in tumors, the selective increase in the intracellular GSSG/2GSH reduction potential in tumors, the selective inhibition of tumor cell ATP production, the selective inhibition of glycolysis in tumor cells, the selective sensitization of tumor cells to DNA-damaging agents, the selective sensitization of tumor cells to DNA-crosslinking agents, and selective cytotoxicity to tumor cells. These effects can be increased by inhibition of GR, an enzyme that reduces GSSG to GSH.

GR Inhibitors

In preferred embodiments of E1 and Ee1, a GR inhibitor is administered before or concurrently with the administration of Agent 1 and Agent 2. More than one GR inhibitor can be used at the same time. In embodiments of Ee1, the GR inhibitor is included in the set of drugs. The GR inhibitor is given systemically at a dose sufficient to inhibit tumor glutathione reductase, preferably before or concurrently with the administration of Agent 1 and Agent 2. A wide range of compounds are known that inhibit GR and can be used; these include BCNU, 2-chloroethylisocyanate; cyclohexyl isocyanate; N,N'-bis(trans-4-hydroxycyclohexyl)-N'-nitrosourea; 2,4-dihydroxybenzylamine; 2-acetylamino-3-[4-(2-acetylamino-2-carboxyethylsulfanylthiocarbonylamino)-phenylthiocarbamoylsulfanyl] propionic acid (2-AAPA); 1-(2-chloroethyl)-3-cyclohexyl-1-nitrosourea (CCNU); hydroxymethylacylfulvene (HMAF); 4,5-dichloro-N-octylisothiazol-3-one (DCOIT); [1-phenyl -2,5-di(2-pyridyl)-phosphole}AuCl]; S-(N-[2-chloroethyl]carbamoyl)glutathione; 5-(N-methylcarbamoyl)glutathione; N-alkymaleimides; S-(N-[2-chloroethyl]carbamoyl)cysteine; and isocyanates. One skilled in the art will know a large number of suitable compounds that inhibit GR. The use of said compounds is within the scope of the present invention. The following references relate to this matter and are hereby incorporated in their entirety by reference: Babson J R, et al., Inactivation of glutathione reductase by 2-chloroethyl nitrosourea-derived isocyanates, Biochem Biophys Res Commun., 1978 Jul. 28, 83(2):754-62; Karplus P A, et al., Inhibition of human glutathione reductase by the nitrosourea drugs 1,3-bis(2-chloroethyl)-1-nitrosourea and 1-(2-chloroethyl)-3-(2-hydroxyethyl)-1-nitrosourea. A crystallographic analysis, Eur J Biochem., 1988 Jan. 15, 171(1-2):193-8; Chresta C M, et al., Depletion of cellular glutathione by N, N'-bis(trans-4-hydroxycyclohexyl)-N'-nitrosourea as a determinant of sensitivity of K562 human leukemia cells to 4-hydroperoxycyclophosphamide, Cancer Res., 1990 Jul. 1, 50(13):4067-71; FitzGerald G B, et al., 2,4-Dihydroxybenzylamine: a specific inhibitor of glutathione reductase, Biochem Pharmacol., 1991 Jan. 15, 41(2):185-90; Seefeldt T, et al., Characterization of a novel dithiocarbamate glutathione reductase inhibitor and its use as a tool to modulate intracellular glutathione, J Biol Chem., 2009 Jan. 30, 284(5):2729-37; Liu X, et al., Profiling patterns of glutathione reductase inhibition by the natural product illudin S and its acylfulvene analogues, Mol Biosyst., 2009 September, 5(9):1013-24; Arning J, et al., Structure-activity relationships for the impact of selected isothiazol-3-one biocides on glutathione metabolism and glutathione reductase of the human liver cell line Hep G2, Toxicology., 2008 Apr. 18, 246(2-3):203-12; Deponte M, et al., Mechanistic studies on a novel, highly potent gold-phosphole inhibitor of human glutathione reductase, J Biol Chem., 2005 May 27, 280(21):20628-37; Jochheim C M, et al., Selective and irreversible inhibition of glutathione reductase in vitro by carbamate thioester conjugates of methyl isocyanate, Biochem Pharmacol., 1994 Mar. 29, 47(7):1197-206; Dubler R E, et al., Simultaneous inactivation of the catalytic activities of yeast glutathione reductase by N-alkylmaleimides, Biochim Biophys Acta., 1981 May 14, 659(1):70-85; Kassahun K, et al., Effect of carbamate thioester derivatives of methyl- and 2-chloroethyl isocyanate on glutathione levels and glutathione reductase activity in isolated rat hepatocytes, Biochem Pharmacol., 1994 Aug. 3, 48(3):587-94.

BCNU

In preferred embodiments, the GR inhibitor is BCNU. In preferred embodiments, the BCNU dose is approximately 50 to 400 mg/m2. In preferred embodiments, the BCNU dose is approximately 50, 75, 100, 125, 150, 175, 200, 225, 250, 275, 300, 325, 350, 375, and 400 mg/m2. Methods for the intravenous administration of BCNU are well known to one skilled in the art. The BCNU is generally administered at no more than approximately 3 mg/m2/min. The following reference relates to this matter and is hereby incorporated in its entirety by reference: Carmustine infusion reactions are more common with rapid administration; Janson B, et al., Support Care Cancer., 2012 October, 20(10):2531-5.

Ethanol

In preferred embodiments of E1 and Ee1, ethanol is administered orally or intravenously to prevent the inactivation of catalase by hydrogen peroxide generated from the reaction of Agent 1 and Agent 2. If the activity of red blood cell catalase is compromised, then hydrogen peroxide can cause hemolysis and methemoglobinemia. In embodiments of Ee1, the ethanol is included in the set of drugs. In preferred embodiments, the ethanol dose is approximately 0.5 to 40 grams. In preferred embodiments, the ethanol dose is approximately, 0.5, 1, 2, 4, 6, 8, 10, 12, 15, 20, 25, 30, 35, and 40 grams. When given intravenously, the ethanol is given over approximately 30 minutes to 6 hours, depending upon the dose. The timing of the ethanol administration is before or concomitant with the administration of Agent 2, so that ethanol is present in the blood during the exposure to hydrogen peroxide. Methods for the intravenous administration of ethanol are well known to one skilled in the art. The following reference relates to this matter and is hereby incorporated in its entirety by reference: FDA prescribing information for 5% Alcohol in 5% Dextrose Injection, USP. The ethanol can also be used as a co-solvent for one or more of the drugs.

DNA-Damaging Agents

The methods and treatment regimens of the present invention can be used to sensitize tumor cells to a wide range of DNA-damaging agents, including chemical and physical DNA-damaging agents. More than one DNA-damaging agent can be used in the same treatment. The specific chemical nature of the DNA-damaging agent is not critical to the mechanisms of action of the present invention. DNA-damaging agents are well known to one skilled in the art and include agents such as radiation, heat, ultrasound, and drugs that induce DNA base damage, DNA single strand breaks, DNA double strand breaks, and DNA crosslinks. Suitable DNA-damaging agents that can be used with the present invention include arsenic trioxide, bendamustine, Bexxar, bleomycin, busulfan, capecitabine, carboplatin, carmustine, chlorambucil, cisplatin, clofarabine, cyclophosphamide, cytarabine, dacarbazine, dactinomycin, daunorubicin, decitabine, doxorubicin, epirubicin, etoposide, fludarabine, fluorouracil, gemcitabine, hydroxyurea, idarubicin, ifosfamide, Irinotecan, lomustine, mechlorethamine, melphalan, mercaptopurine, mitomycin C, olaparib, oxaliplatin, palbociclib, procarbazine, radium 223 dichloride, temozolomide, thioguanine, thiotepa, topotecan, trabectedin, and vincristine. One skilled in the art will recognize and know a large number of DNA-damaging agents; the use of said agents with the present methods is within the scope of the present invention. The dose of said DNA-damaging agent employed in this method would generally be between 50 to 100% of that typically used in the treatment of cancer in the particular clinical setting (e.g., in the setting of stem cell infusion).

DNA-Crosslinking Agents

In preferred embodiments of E1 and Ee1, the DNA-damaging agent is a DNA-crosslinking drug. DNA-crosslinking agents include bendamustine, bizelesin, busulfan, busulfan, carboplatin, carboplatin, carmustine, chlorambucil, cisplatin, cisplatin, cyclophosphamide, ifosfamide, lomustine, mechlorethamine, melphalan, mitomycin c, nedaplatin, oxaliplatin, oxaliplatin, picoplatin, satraplatin, thiotepa. Analogs, derivatives, and prodrugs of these cross-linking agents are also within the scope of the present invention. Additional suitable DNA-crosslinking agents are described in the following reference, which is hereby incorporated by reference in its entirety: Raj ski S R, et al., DNA Cross-Linking Agents as Antitumor Drugs, Chem Rev., 1998 Dec. 17, 98(8):2723-2796. Techniques for administering said DNA-crosslinking drugs are well known to one skilled in the art. The following reference relates to this matter and is hereby incorporated in its entirety by reference: Pazdur R, et al., A Multidisciplinary Approach. Medical, Surgical and Radiation Oncology-13th ed., 2010, Publisher: Matthews Medical Books. One skilled in the art will recognize and know a large number of DNA-crosslinking agents; the use of said agents with the present methods is within the scope of the present invention. The dose of said agents employed in this method would generally be between 30 to 100% of that typically used in the treatment of cancer in the particular clinical setting (e.g., in the setting of stem cell infusion).

Melphalan

In preferred embodiments, the DNA-crosslinking drug is melphalan in a dose range of approximately 10 mg/m2 to 200 mg/m2. In preferred embodiments, the melphalan dose is approximately 10, 20, 30, 40, 50, 60, 70, 80, 90, 100, 110, 120, 130, 140, 150, 160, 170, 180, 190, and 200 mg/m2. Methods for the intravenous administration of melphalan are well known to one skilled in the art. The melphalan is administered over a period of approximately 5 to 60 minutes. The melphalan is administered either immediately before, concomitantly with, or immediately after Agent 1 and Agent 2.

Bone Marrow Stem Cell Infusions

In preferred embodiments, bone marrow stem cells are infused to reverse bone marrow toxicity from the DNA-damaging drug. Stem cell infusions are generally given if the melphalan dose exceeds approximately 50 mg/m2 or the BCNU dose exceeds approximately 200 mg/m2 or if the patient has, or is expected to have, prolonged bone marrow suppression following the drug treatment. The stem cells are collected prior to the administration of the chemotherapy drugs (i.e., the DNA-damaging drugs) and are purified and stored. The bone marrow stem cells are preferably infused 1-2 days after the chemotherapy drugs; however, the stem cells can be administered at later times. Purified autologous bone marrow stem cells are strongly preferred; however, allogeneic bone marrow stem cells can also be employed. Technology for hematopoietic stem cell collection, purification, storage, and transplantation or infusion are well known to one skilled in the art. The use of purified stem cell preparations enriched for CD34+ hematopoietic cells and depleted of circulating tumor cells is preferred. The following references relate to this matter and are hereby incorporated in their entirety by reference: Mapara M Y, et al., Exp Hematol., 1999 January, 27(1):169-75; Mohr M, et al., Clin Cancer Res., 1999 May, 5(5):1035-40; Cellular, Tissue and Gene Therapies Advisory Committee, Meeting Date of Sep. 23, 2011, CliniMACS® CD34 Reagent System, Briefing Package, HUD #04-0146, HDE #BH110018, U.S. Food and Drug Administration.

Mechanisms of Selective Drug Delivery to Tumors

The mechanism by which Agent 1 and Agent 2 will selectively deliver Drug 1 to tumors is unexpected, as there would appear to be no basis for tumor selectivity: both agents will distribute essentially uniformly throughout the extravascular fluid after systemic administration, and furthermore the rate of the reaction to form Drug 1 will be essentially equal throughout the extracellular space both in tumor and in normal tissues. It would therefore seem that there is no basis for tumor selectivity in drug delivery. However, the system of Agent 1, Agent 2, and Drug 1 has unexpected pharmacokinetic properties that can give up to a 20-fold increased drug delivery to tumors. This is especially unexpected because tumors have decreased blood flow and increased interstitial fluid pressure compared to normal tissues, which generally serve as barriers to drug delivery into tumors. The present invention exploits these well-known "barriers" to drug delivery to tumors to paradoxically enhance drug delivery to tumors.

One mechanism of action of the embodiment E1 is as follows: Normally interstitial fluid pressure is about −3 to −6 mmHg relative to atmospheric pressure. In tumors, the interstitial fluid pressure is significantly greater. The increased interstitial fluid pressure of tumors is due to leaky capillaries that allow extravasation of albumin into the intestinal space (which increases the oncotic pressure in the extracellular fluid), decreased or absent lymph flow, dysregulation of the tumor blood flow (which can lead to higher capillary blood pressure in tumors), and increased production of osmotically active substances such as hyaluronic acid within the tumor microenvironment. When the interstitial fluid pressure increases above 0, there is a large increase in interstitial fluid volume. Accordingly, tumors are characterized by a large increase in interstitial fluid volume compared to normal tissues. The ratio of interstitial fluid volume to intracellular fluid volume is much greater in tumors than in normal tissues: typically, approximately 3 to 12 times greater in tumors than in most normal tissues. The following references relate to this matter and are hereby incorporated by reference in their entirety: Munson J M, et al., Interstitial fluid flow in cancer: implications for disease progression and treatment, Cancer Manag Res., 2014 Aug. 19, 6:317-28; Baronzio G, et al., Overview of Methods for Overcoming Hindrance to Drug Delivery to Tumors, with Special Attention to Tumor Interstitial Fluid., Front Oncol., 2015 Jul. 23, 5:165; Less J R, et al., Interstitial hypertension in human breast and colorectal tumors, Cancer Res., 1992 Nov. 15, 52(22):6371-4; Nathanson S D, et al., Interstitial fluid pressure in breast cancer, benign breast conditions, and breast parenchyma, Ann Surg Oncol., 1994 July, 1(4):333-8; Guyton A C, Interstitial Fluid Pressure. II. Pressure-Volume Curves of Interstitial Space, Circ Res., 1965 May, 16:452-60; Gullino P M, et al., The Interstitial Water Space of Tumors, Cancer Res., 1965 June, 25:727-31; O'Connor S W, et al., Accessibility of circulating immunoglobulin G to the extravascular compartment of solid rat tumors, Cancer Res., 1984 September, 44(9):3719-23; Boucher Y, et al., Tumor angiogenesis and interstitial hypertension, Cancer Res., 1996 Sep. 15, 56(18):4264-6.

After the intravenous or systemic administration of Agent 1 and Agent 2, there will be a rapid equilibration of the concentrations of the agents between the plasma and interstitial fluid. After the distributive phase is complete, there will be essentially no net flux of Agent 1 or Agent 2 between the plasma and interstitial fluid (except for that resulting from gradients generated by renal elimination of Agent 1 and Agent 2 from plasma). If the rate of renal clearance of Agent 1 and Agent 2 is small compared to the production rate of Drug 1, then its effect will be small. Since the production rate of Drug 1 will be essentially equal in both the plasma and interstitial fluid any net flux of Drug 1 between the plasma and interstitial fluid would result only from concentration gradients that result from differences in the elimination rates in the respective compartments. Since Drug 1 is both rapidly degraded in the intravascular compartment and rapidly taken up from interstitial fluid into intracellular water, the absolute concentration of Drug 1 in both the plasma and interstitial fluid will be low, and the absolute magnitude of any concentration gradients between plasma and interstitial fluid will also be low. Absent a significant concentration gradient between plasma and interstitial fluid, Drug 1 in the interstitial fluid will largely be taken up into the intracellular space in the microenvironment where it is formed. In this case, the dose of Drug 1 received by cells at a particular site will depend upon the ratio of interstitial fluid to intracellular fluid at the site. Since this ratio is much higher in tumors, tumors cells will receive a correspondingly greater dose of Drug 1 than cells in normal tissues. (The same will apply for Drug 2.)

In certain situations, Drug 1 will degrade much faster in the intravascular space than in the interstitial fluid. In addition, in certain situations the diffusion or uptake of Drug 1 from interstitial fluid into the intravascular space can be much faster than the uptake of Drug 1 into the intracellular space. For example, this will be the case when Drug 1 is hydrogen peroxide, which is rapidly decomposed in the intravascular space. The rate-limiting step is the diffusion of hydrogen peroxide into red blood cells, where it is decomposed by catalase. Hydrogen peroxide in the intravascular space is rapidly destroyed by catalase: the half-life is 50 milliseconds. By contrast, the half-life of hydrogen peroxide decomposition by pancreatic cancer cells in a tumor will be about 1.4 seconds. This estimate is based on extrapolation from the known rates of hydrogen peroxide consumption by pancreatic cancer cells in vitro to in vivo cell densities. The rate of efflux of hydrogen peroxide out of the interstitial fluid into the intravascular compartment will be a function of the surface area of the capillaries per ml of interstitial fluid and the volume of red blood cells (in the capillaries) per ml of interstitial fluid, both of which are much higher in normal tissues than in tumors. For example, the ratio of RBC volume to interstitial fluid volume in rat fibrosarcomas is ~0.0047; the ratio is ~66 times higher in rat lung, 40 times higher in rat kidney, and ~32 times higher in the heart. The capillary surface area/ml of interstitial fluid is also much smaller in tumors than in most normal tissues. In many normal tissues, the ratios of red blood cell volume/interstitial fluid volume and capillary surface area/interstitial fluid volume are so high that nearly all hydrogen peroxide will be consumed in the intravascular space and the dose of hydrogen peroxide delivered to the intracellular space of the normal tissue will be very small compared to that delivered to the intracellular space of tumors.

The following references relate to this matter and are hereby incorporated by reference in their entirety: Wagner B A, et al., An Assay for the Rate of Removal of Extracellular Hydrogen Peroxide by Cells, Redox Biol., 2013, 1(1):210-217; O'Connor S W, et al., Accessibility of circulating immunoglobulin G to the extravascular compartment of solid rat tumors, Cancer Res., 1984 September, 44(9):3719-23; Dobson G P, et al., Intracellular, interstitial and plasma spaces in the rat myocardium in vivo, J Mol Cell Cardiol., 1997 December, 29(12):3357-63; Jain R K, Transport of molecules across tumor vasculature, Cancer Metastasis Rev., 1987, 6(4):559-93.

Mechanism of Action of DHA

The oxidation of ascorbic acid, which is catalyzed by hydroxocobalamin, generates DHA. DHA is rapidly taken up by cells and reduced to ascorbic acid; in the process 2 GSH molecules are oxidized to GSSG. DHA is transported into cells by GLUT transporters, which are highly overexpressed on cancer cells. DHA and its decomposition product 2,3-DKG are highly electrophilic and can mediate useful pharmacologic effects in cancer cells such as inhibiting mitosis, depleting intracellular GSH, increasing the intracellular GSSG/2GSH reduction potential in tumor cells, inhibiting glycolysis, depleting ATP, and killing tumor cells. The following references relate to this matter and are hereby incorporated in their entirety by reference: Spielholz C, et al., Increased facilitated transport of dehydroascorbic acid without changes in sodium-dependent ascorbate transport in human melanoma cells, Cancer Res., 1997 Jun. 15, 57(12): 2529-37; Barron C C, et al., Facilitative glucose transporters: Implications for cancer detection, prognosis and treatment; Metab. Clin. Exp., 2016 February, 65(2):124-39; Gambhir S S, et al., A tabulated summary of the FDG PET literature, J Nucl Med., 2001 May, 42(5 Suppl):1S-93S; Poydock M E, et al., Mitogenic inhibition and effect on survival of mice bearing L1210 leukemia using a combination of dehydroascorbic acid and hydroxycobalamin, Am J Clin Oncol., 1985 June, 8(3):266-9; Yun J, et al., Vitamin C selectively kills KRAS and BRAF mutant colorectal cancer cells by targeting GAPDH, Science, 2015 Dec. 11, 350 (6266):1391-6.

Mechanism of Action of Hydrogen Peroxide

Hydrogen peroxide in the presence of transition metals generates reactive oxygen species that can damage DNA and cellular components. Hydrogen peroxide can also induce oxidative stress, deplete intracellular GSH, increase the intracellular GSSG/2GSH reduction potential in tumor cells, inhibit glycolysis, deplete ATP, sensitize cells to DNA-damaging agents, and cause cytotoxicity. The effects are increased by high intracellular levels of ascorbic acid, which elevate free iron levels in cells. Inhibition of GR also increases the effects of hydrogen peroxide. The following references relate to this matter and are hereby incorporated in their entirety by reference: Nakamura J, et al., Micromolar concentrations of hydrogen peroxide induce oxidative DNA lesions more efficiently than millimolar concentrations in mammalian cells, Nucleic Acids Res., 2003, Mar. 15, 31(6):1790-5; Byrnes R W, Evidence for involvement of multiple iron species in DNA single-strand scission by H2O2 in HL-60 cells, Free Radic Biol Med., 1996, 20(3):399-406; Nathan C F, et al., Antitumor effects of hydrogen peroxide in vivo, J Exp Med., 1981 Nov. 1, 154(5):1539-53; Kurz T, et al., Lysosomal redox-active iron is important for oxidative stress-induced DNA damage, Ann N Y Acad Sci., 2004 June, 1019:285-8; LaCagnin L B, et al., Metabolic changes in alveolar type II cells after exposure to hydrogen peroxide, Am J Physiol., 1990 August, 259(2 Pt 1):L57-65; Colussi C, et al., H2O2-induced block of glycolysis as an active ADP-ribosylation reaction protecting cells from apoptosis, FASEB J., 2000 November, 14(14):2266-76; Duarte T L, et al., Vitamin C modulation of H2O2-induced damage and iron homeostasis in human cells, Free Radic Biol Med., 2007 Oct. 15, 43(8):1165-75; Nathan C F, et al., Tumor cell anti-oxidant defenses. Inhibition of the glutathione redox cycle enhances macrophage-mediated cytolysis, J Exp Med., 1981 Apr. 1, 153(4):766-82; Jahngen-Hodge J, et al., Regulation of ubiquitin-conjugating enzymes by glutathione following oxidative stress, J Biol Chem., 1997 Nov. 7, 272 (45):28218-26.

Mechanisms of Action of Glutathione Reductase Inhibition

The concentration of GSH in cells is typically in the range of 0.5 to 10 mM. When GSH is oxidized, the GSSG formed is rapidly reduced back into GSH by glutathione reductase. Cells have a tremendous capacity to reduce GSSG. For example, the reductive capacity of hepatocyte cells for GSSG in vitro is ~250 mmoles/hour per liter of intracellular fluid. In order to depress intracellular GSH levels, it is necessary to oxidize GSH at a rate that exceeds the cellular reductive capacity for GSSG. This would generally require the delivery of an enormous and impractical quantity of oxidizing agent. The addition of a glutathione reductase inhibitor prevents the reduction of GSSG and thereby allows intracellular GSH levels to be decreased by low levels of oxidizing agents such as hydrogen peroxide. The following reference relates to this matter and is hereby incorporated in its entirety by reference: Tribble D L, et al., Oxygen dependence of oxidative stress. Rate of NADPH supply for maintaining the GSH pool during hypoxia, Biochem Pharmacol., 1990 Feb. 15, 39(4):729-36.

List A: Types of Cancer that can be Treated

Metastatic cancers that can be treated with the methods and treatment regimens and embodiments of the present invention include: Metastatic cancer, Refractory metastatic cancer, BRCA1-related metastatic cancer (inherited mutation), BRCA2-related metastatic cancer (inherited mutation), PALB2-related metastatic cancer (inherited mutation), Metastatic cancer in the setting of an inherited BRCA/Fanconi pathway mutation(s), Metastatic cancer in the setting of an acquired BRCA/Fanconi pathway mutation(s), BRCA2-related pancreatic cancer (inherited mutation), BRCA2-related prostate cancer (inherited mutation), BRCA2-related ovarian cancer (inherited mutation), BRCA2-related breast cancer (inherited mutation), BRCA2-related fallopian tube cancer (inherited mutation), BRCA1-related pancreatic cancer (inherited mutation), BRCA1-related prostate cancer (inherited mutation), BRCA1-related ovarian cancer (inherited mutation), BRCA1-related fallopian tube cancer (inherited mutation), BRCA1-related breast cancer (inherited mutation), PALB2-related pancreatic cancer (inherited mutation), PALB2-related prostate cancer (inherited mutation), PALB2-related ovarian cancer (inherited mutation), PALB2-related fallopian tube cancer (inherited mutation), PALB2-related breast cancer (inherited mutation), Breast cancer (ductal adenocarcinoma), RAD50-related breast cancer (inherited mutation), Cancers that arise in patients with an inherited germline mutation(s) or an acquired somatic mutation(s) in a gene or genes involved in DNA crosslink repair, homologous recombination, and/or DNA repair, Breast cancer (lobular adenocarcinoma), Breast cancer (sarcoma), Breast cancer (triple negative), Breast cancer (inflammatory), Breast cancer (Paget's), Prostate cancer (adenocarcinoma), Pancreatic cancer (adenocarcinoma, Stage I-IV), Ovarian cancer (serous), Ovarian cancer (endometroid), Ovarian cancer (clear cell), Ovarian cancer (mucinous), Adenocarcinoma, Basal Cell Carcinoma, Bile Duct cancer, Bladder cancer, Bronchial cancer, Carcinoid Tumor, Cervical cancer (squamous), Cervical cancer (adenocarcinoma), Colorectal cancer, Colon cancer, Duodenal cancer, Endometrial cancer, Endometroid endometrial cancer, Esophageal cancer, Esophageal cancer (squamous cell), Esophageal cancer (adenocarcinoma), Ewing sarcoma, Fallopian tube cancer, Ocular melanoma, Malignant fibrous histiocytoma of bone, Osteosarcoma, Gallbladder cancer, Gastric cancer, Gastrointestinal carcinoid tumor, Gastrointestinal stromal tumors (GIST), Germ cell tumors, Head and neck cancer, Hepatocellular cancer, Hypopharyngeal cancer, Malignant islet cell tumors, Renal cell carcinoma, Laryngeal cancer, Lip and oral cavity cancer, Leiomyosarcomas, Lymphoma, Leukemia, T cell leukemia, B-cell lymphoma, B-cell leukemia, Acute myelogenous leukemia, Myeloma, Non-Hodgkins lymphoma, Lung cancer, Non-small cell lung cancer, Small cell lung cancer, Lung cancer (adenocarcinoma), Lung cancer (large cell), Lung cancer (squamous cell), Melanoma, Merkel cell carcinoma, Mesothelioma, Nasal cavity and paranasal sinus cancer, Nasopharyngeal cancer, Neuroendocrine cancer, Oral cancer, Oropharyngeal cancer, Pancreatic neuroendocrine tumors, Paranasal sinus and nasal cavity cancer, Parathyroid cancer, Penile cancer, Pharyngeal cancer, Pheochromocytoma, Rectal cancer, Renal cell cancer, Renal clear cell cancer, Renal chromophobe cancer, Renal papillary cancer, Renal pelvis and ureter, Transitional cell cancer, Salivary gland cancer, Sarcoma, Squamous cell carcinoma, Rhabdomyosarcoma, Small intestine cancer, Soft tissue sarcoma, Squamous neck cancer with occult primary, Testicular cancer, Thyroid cancer (papillary, follicular, medullary, and anaplastic), Transitional cell cancer of the renal pelvis and ureter, Urethral cancer, Uterine cancer, Undifferentiated cancer, Endometrial uterine Sarcoma, Vaginal cancer, and Vulvar cancer. The cancer treatment methods of the present invention can be used to treat, but are not limited to treating, cancers that arise in patients with an inherited germline mutation(s) or an acquired somatic mutation(s) in ATR, BARD1, BLM, BRCA1, BRCA2, BRIP 1 (FANCJ, BACH1), EME1, ERCC1, ERCC4, FAN1, FANCA, FANCB, FANCC, FANCD1, FANCD2, FANCE, FANCF, FANCG, FANCI, FANCJ, FANCL, FANCM, FANCN, FANCO, FANCP, FANCQ, FANCQ, FANCR, FANCS, FANCT, HELQ, MEN1, MUS81, NBN (NBS1), PALB2, RAD50, RAD51 (FANCR), RAD51C (FANCO), RAD51D, REV1, SLX4 (FANCP), UBE2T (FANCT), USP1, WDR48, XPF, XRCC2, XRCC3, or other genes involved in DNA-crosslink repair, homologous recombination, or DNA repair.

The above gene names are based on the HUGO Human Genome Nomenclature System, which is well known to one skilled in the art. Cancer cells with an inherited or acquired mutation(s) in the above genes have an increased sensitivity to DNA-damaging and especially DNA-crosslinking agents. Methods for identifying such inherited and somatic tumor mutations are well known to one skilled in the art. More detailed descriptions of metastatic cancers, all of which are within the scope of the present invention, are provided in the following reference: Holland-Frei Cancer Medicine, 6th edition, Edited by Kufe D W, et al., BC Decker Inc., Hamilton, Ontario.

Mechanisms of Sensitization to DNA-Damaging Agents

The applicability of the present invention to sensitizing cells to DNA-crosslinking agents is due to the common mechanisms of GSH-mediated detoxification of electrophiles and the common mechanisms involved in the repair of DNA interstrand crosslinks, regardless of the particular crosslinking agent. The following reference relates to this matter and is hereby incorporated in its entirety by reference: Raj ski S R, et al., Chem Rev., 1998 Dec. 17, 98(8):2723-2796. The applicability of the present invention to sensitizing tumor cells to DNA-damaging agents in general is the result of the multiple mechanisms of DNA repair that are inhibited by an increase in the intracellular GSH reduction potential. This will result in a profound synergy: the antitumor activity of the drug combinations of the present invention is greater than the additive antitumor activity of the individual drugs.

Multiple steps required for the repair of DNA-drug monoadducts and DNA interstrand crosslinks are redox sensitive and are inhibited by an increase in the intracellular GSSG/2GSH reduction potential. This explains the profound hypersensitivity to melphalan induced by oxidative stress seen with BCNU and adriamycin. The following references relate to this matter and are hereby incorporated in their entirety by reference: Jevtović-Todorović V, et al., J Cancer Res Clin Oncol., 1991, 117(4):313-20; Jevtović-Todorović V, et al., Biochem Pharmacol., 1992 Oct. 6, 44(7):1383-93.

Oxidative stress and an increase in the intracellular GSSG/2GSH reduction potential can inhibit proteins involved in DNA repair by a variety of mechanisms, including S-glutathionylation of the proteins, intermolecular disulfide formation, intramolecular disulfide formation, and by impairing the detoxification of ROS, which causes an increase in levels of ROS that oxidize critical protein thiols. In addition, it can compromise cellular energy production. An increase the intracellular GSSG/2GSH reduction potential leads to global changes in cellular metabolism that affect thousands of redox-sensitive proteins. Redox-sensitive proteins are required for all major pathways of DNA repair.

The enzyme MGMT detoxifies BCNU by catalyzing removal of the drug adducts from guanine bases in DNA. MGMT is a redox-sensitive enzyme, which is dependent upon an active-site cysteine that is glutathionylated and inhibited under oxidative conditions. The following reference relates to this matter and is hereby incorporated in its entirety by reference: Niture S K, et al., Human MGMT is a prime target for inactivation by oxidative stress, mediated by glutathionylation and oxidation of the active-site cysteine145, Proc. Am. Assoc. Cancer Res., 2005, 46:857.

Ubiquitylation, SUMOylation, and neddylation are critical to multiple steps in multiple pathways of DNA repair, including nucleotide excision repair (NER), homologous recombination (HR), single strand annealing (SSA), non-homologous end joining (NHEJ), alternate NHEJ, and translesion DNA synthesis. Multiple steps in the enzymatic pathways of ubiquitylation, SUMOylation, and neddylation are dependent upon active-site cysteines that are redox sensitive and inhibited by glutathionylation and oxidation of the active sites. The following references relate to this matter and are hereby incorporated in their entirety by reference: Bossis G, et al., Regulation of SUMOylation by reversible oxidation of SUMO conjugating enzymes, Mol Cell., 2006 Feb. 3, 21(3):349-57; Kumar A, et al., The bacterial fermentation product butyrate influences epithelial signaling via reactive oxygen species-mediated changes in cullin-1 neddylation, J Immunol., 2009 Jan. 1, 182(1):538-46; Jahngen-Hodge J, et al., Regulation of ubiquitin-conjugating enzymes by glutathione following oxidative stress, J Biol Chem., 1997 Nov. 7, 272(45):28218-26; Obin M, et al., Redox regulation of ubiquitin-conjugating enzymes: mechanistic insights using the thiol-specific oxidant diamide, FASEB J., 1998 May, 12(7):561-9; Nouspikel T, Multiple roles of ubiquitination in the control of nucleotide excision repair, Mech Ageing Dev., 2011 August, 132(8-9):355-65; Ramadan K, et al., Degradation-linked ubiquitin signal and proteasome are integral components of DNA double strand break repair: New perspectives for anti-cancer therapy, FEBS Lett., 2011 Sep. 16, 585(18):2868-75; Bekker-Jensen S, et al., The ubiquitin- and SUMO-dependent signaling response to DNA double-strand breaks, FEBS Lett., 2011, Sep. 16, 585(18):2914-9; Kee Y, et al., Inhibition of the Nedd8 system sensitizes cells to DNA interstrand cross-linking agents, Mol Cancer Res., 2012 March, 10(3):369-77; Cukras S, et al., Inactivating UBE2M impacts the DNA damage response and genome integrity involving multiple cullin ligases, PLoS One., 2014 Jul. 15, 9(7):e101844; Al-Hakim A, The ubiquitous role of ubiquitin in the DNA damage response, DNA Repair (Amst), 2010 Dec. 10, 9(12):1229-40.

Ku protein is required for the NHEJ repair of DNA double stranded breaks and is redox sensitive. Oxidative stress also inhibits DNA-dependent protein kinase (DNA-PKcs) and inhibits the localization of DNA-PKcspThr2609 at double stranded breaks and impairs repair. The following references relate to this matter and are hereby incorporated in their entirety by reference: Zhang W W, Biochem J., 1993 Aug. 1, 293(Pt 3):769-74; Mladenov E, et al., Induction and repair of DNA double strand breaks: the increasing spectrum of non-homologous end joining pathways, Mutat Res., 2011 Jun. 3, 711(1-2):61-72; Bacsi A, et al., Modulation of DNA-dependent protein kinase activity in chlorambucil-treated cells, Free Radic Biol Med., 2005 Dec. 15, 39(12):1650-9; Boldogh I, et al., Reduced DNA double strand breaks in chlorambucil resistant cells are related to high DNA-PKcs activity and low oxidative stress, Toxicology, 2003 Nov. 15, 193(1-2):137-52.

Topoisomerase II is involved in DNA unwinding, is involved in multiple steps of DNA repair, and is redox sensitive. The following references relate to this matter and are hereby incorporated in their entirety by reference: Li T K, et al., Activation of topoisomerase II-mediated excision of chromosomal DNA loops during oxidative stress, Genes Dev., 1999 Jun. 15, 13(12):1553-60; Wang H, et al., Stimulation of topoisomerase II-mediated DNA damage via a mechanism involving protein thiolation, Biochemistry, 2001 Mar. 20, 40(11):3316-23, Kawiak A, et al., Induction of apoptosis by plumbagin through reactive oxygen species-mediated inhibition of topoisomerase II, Toxicol Appl Pharmacol., 2007 Sep. 15, 223(3):267-76; Pu Q Q, et al., Induction of alkylator (melphalan) resistance in HL60 cells is accompanied by increased levels of topoisomerase II expression and function, Mol Pharmacol., 1999 July, 56(1): 147-53.

XPA is required for NER, and XPA deficiency sensitizes cells to melphalan. XPA is redox sensitive. The following references relate to this matter and are hereby incorporated in their entirety by reference: Smirnova J, et al., Quantitative electrospray ionization mass spectrometry of zinc finger oxidation: the reaction of XPA zinc finger with H2O2, Anal Biochem., 2007 Oct. 15, 369(2):226-31; Smirnova J, et al., Reaction of the XPA zinc finger with S-nitrosoglutathione, Chem Res Toxicol., 2008 February, 21(2):386-92.

RPA is required for all major DNA repair pathways and is redox sensitive. The following references relate to this matter and are hereby incorporated in their entirety by reference: Zou Y, et al., Functions of human replication protein A (RPA): from DNA replication to DNA damage and stress responses, J Cell Physiol, 2006 August, 208(2):267-73; Park J S, et al., Zinc finger of replication protein A, a non-DNA binding element, regulates its DNA binding activity through redox, J Biol Chem., 1999 Oct. 8, 274(41): 29075-80; Wang M, et al., Role of zinc-finger motif in redox regulation of human replication protein A, Antioxid Redox Signal., 2001 August, 3(4):657-69; Cooper A J, et al., Reversible and irreversible protein glutathionylation: biological and clinical aspects, Expert Opin Drug Metab Toxicol, 2011 July, 7(7):891-910, Epub 2011 May 11.

Deubiquitinases (DUB) are critical to multiple pathways of DNA repair and are redox sensitive. The following references relate to this matter and are hereby incorporated in their entirety by reference: Lee J G, et al., Reversible inactivation of deubiquitinases by reactive oxygen species in vitro and in cells, Nat Commun. 2013, 4:1568; Jacq X, et al., Deubiquitylating enzymes and DNA damage response pathways, Cell Biochem Biophys., 2013 September, 67(1):25-43; Oestergaard V H, et al., Deubiquitination of FANCD2 is required for DNA crosslink repair, Mol Cell., 2007 Dec. 14, 28(5):798.

XRCC3 is essential to multiple steps of HR; XRCC3 deficiency is characterized by extreme hypersensitivity to DNA-crosslinking agents. The protein has multiple cysteine groups that are redox sensitive, susceptible to modification by electrophilic thiol reactive agents and glutathionylation. The following references relate to this matter and are hereby incorporated in their entirety by reference: Nikolova T, et al., Chloroethylnitrosourea-induced cell death and genotoxicity: cell cycle dependence and the role of DNA double-strand breaks, HR and NHEJ., Cell Cycle, 2012 Jul. 15, 11(14): 2606-19; Pierre-Marie G, et al., Oxidative Stress in Mammalian Cells Impinges on the Cysteines Redox State of Human XRCC3 Protein and on Its Cellular Localization, PLoS One., 2013, 8(10): e75751.

Ribonucleotide Reductase (RNR) has critical cysteine groups and is a redox-sensitive enzyme involved in DNA damage repair. The following reference relates to this matter and is hereby incorporated in its entirety by reference: Holmgren A, et al., The use of thiols by ribonucleotide reductase, Free Radic Biol Med., 2010 Dec. 1, 49(11):1617-28.

Human apurinic/apyrimidinic (AP) endonuclease 1 (APE1) is a redox-sensitive enzyme that plays a key role in DNA base excision repair pathways. The following reference relates to this matter and is hereby incorporated in its entirety by reference: Kim Y J, et al., S-glutathionylation of cysteine 99 in the APE1 protein impairs abasic endonuclease activity, J Mol Biol., 2011 Dec. 2, 414(3):313-26.

ATP is required for multiple steps in DNA repair. Multiple critical enzymes involved in ATP production are redox-sensitive and are inhibited by oxidative stress. Aconitase is a redox-sensitive enzyme involved in energy production in the Krebs cycle. Glyceraldehyde 3-phosphate dehydrogenase is a redox-sensitive enzyme that is essential for ATP production by glycolysis. The mitochondrial carnitine/acylcarnitine carrier (CAC) is redox sensitive: it is required for the transport of acylcarnitines into mitochondria and the β-oxidation of fatty acids, which is an important source of ATP for prostate cancer cells. α-Ketoglutarate dehydrogenase (KGDH) is a redox-sensitive enzyme critical to energy generation in the Krebs cycle. Isocitrate dehydrogenase is a redox-sensitive enzyme in the Krebs cycle. The following reference relates to this matter and is hereby incorporated in its entirety by reference: Lushchak O V, et al., Aconitase post-translational modification as a key in linkage between Krebs cycle, iron homeostasis, redox signaling, and metabolism of reactive oxygen species, Redox Rep., 2014 January, 19(1):8-15; Brodie A E, et al., Cellular recovery of glyceraldehyde-3-phosphate dehydrogenase activity and thiol status after exposure to hydroperoxides, Arch Biochem Biophys., 1990 January, 276(1):212-8; Brodie A E, et al., Reversible oxidation of glyceraldehyde 3-phosphate dehydrogenase thiols in human lung carcinoma cells by hydrogen peroxide, Biochem Biophys Res Commun., 1987 Oct. 14, 148(1):120-5; Giangregorio N, et al., Glutathione controls the redox state of the mitochondrial carnitine/acylcarnitine carrier Cys residues by glutathionylation, Biochim Biophys Acta., 2013 November, 1830(11):5299-304; Liu Y, Fatty acid oxidation is a dominant bioenergetic pathway in prostate cancer, Prostate Cancer Prostatic Dis., 2006, 9(3):230-4; McLain A L, et al., Glutathionylation of α-ketoglutarate dehydrogenase: the chemical nature and relative susceptibility of the cofactor lipoic acid to modification, Free Radic Biol Med., 2013 August, 61:161-9; Kil I S, et al., Regulation of mitochondrial NADP+-dependent isocitrate dehydrogenase activity by glutathionylation, J Biol Chem., 2005 Mar. 18, 280(11):10846-54

Protein tyrosine phosphatases (PTPs) are involved in multiple pathways of DNA repair and are redox-sensitive enzymes. The following reference relates to this matter and is hereby incorporated in its entirety by reference: Sohn J, et al., Catalytic and chemical competence of regulation of cdc25 phosphatase by oxidation/reduction, Biochemistry., 2003 Sep. 2, 42(34):10060-70

There are many other redox-sensitive enzymes and proteins in addition to those listed above that are critical to the repair of DNA damage and that are inhibited by oxidative stress and that will be inhibited in tumors by the present invention, including by the combination of BCNU, hydroxocobalamin, and ascorbic acid.

Mechanism of Catalase Protection by Ethanol

The role of the ethanol is to prevent the inactivation of red blood cell catalase. The intravascular decomposition of hydrogen peroxide in the setting of glutathione reductase inhibition is dependent upon the enzymatic activity of red blood cell catalase. Catalase can exist in a number of forms. Hydrogen peroxide oxidizes the heme iron of the resting form of catalase (i.e., ferricatalase) to an oxyferryl group with a porphyrin radical called Compound I, in the process creating one molecule of water. Compound I then oxidizes another molecule of hydrogen peroxide, regenerating the ferricatalase form of catalase, and in the process, creates one molecule of oxygen and another molecule of water. The net result is that the 2 molecules of hydrogen peroxide are converted by the catalase into one molecule of molecular oxygen and two molecules of water. Compound I, however, can also be reduced by a single electron to Compound II, which is an inactive form of catalase. NADPH binds to catalase and inhibits the formation of Compound II. Glucose-6 phosphate dehydrogenase (G6PD) deficiency, which is a common inherited genetic disorder, impairs NADPH production and can result in accumulation of Compound II and catalase inhibition. This can lead to hemolysis or methemoglobinemia under conditions of oxidative stress. Acquired G6PD deficiency or impaired NADPH production would lead to the same result. Low concentrations of ethanol are able to prevent the inactivation of catalase by converting Compound I into ferricatalase; in the process the ethanol is oxidized to acetaldehyde. The following references relate to this matter and are hereby incorporated in their entirety by reference: Kirkman H N, et al., Mammalian catalase: a venerable enzyme with new mysteries, Trends Biochem Sci., 2007 January, 32(1):44-50; Kirkman H N, et al., The function of catalase-bound NADPH, J Biol Chem., 1987 Jan. 15, 262(2):660-6; Kirkman H N, et al., Mechanisms of protection of catalase by NADPH. Kinetics and stoichiometry, J Biol Chem., 1999 May 14, 274(20):13908-14;

Method to Protect Catalase Subjects

The scope of the present invention includes methods to prevent the loss of catalase function and to prevent oxidant-induced hemolysis and/or methemoglobin formation in subjects treated with oxidant drugs or agents that generate hydrogen peroxide; said methods comprise the systemic administration of ethanol. The ethanol is administered prior to or during exposure to the oxidant. The dose of ethanol is in the approximate range of 500 mg to 40 grams. The ethanol can be given orally or intravenously. In a preferred embodiment, the dose of ethanol is approximately 3 to 6 grams/m2, given over approximately 1 hour intravenously. The drug can also be given as a constant intravenous infusion for longer periods of time.

Embodiment E2

The present invention also relates to a method for the treatment and effective treatment of metastatic cancer and refractory metastatic cancer. The method, referred to as embodiment E2, comprises the following:
a. The administration of melphalan; and
b. The administration of BCNU; and
c. The administration hydroxocobalamin; and
d. The administration of ascorbic acid; and
e. Optionally administering ethanol; and
f. Optionally administering bone marrow stem cells.

Embodiment Ee2

Embodiment Ee2 of the present invention is a set of drugs for use in a regimen for the treatment and effective treatment of metastatic cancer and refractory metastatic cancer. The set of drugs comprises:
a. Melphalan; and
b. BCNU; and
c. Hydroxocobalamin; and
d. Ascorbic acid; and
e. Optionally ethanol.
The treatment regimen comprises:
a. The administration of melphalan; and
b. The administration of BCNU; and
c. The administration hydroxocobalamin; and
d. The administration of ascorbic acid; and
e. Optionally administering ethanol; and
f. Optionally administering bone marrow stem cells.

Cancers that can be Treated

The cancers that can be treated with embodiments E2 and Ee2 are as described in LIST A.

Bone Marrow Stem Cell Infusions

In preferred embodiments, bone marrow stem cells are infused to reverse bone marrow toxicity. Stem cell infusions are generally given if the melphalan dose exceeds approximately 50 mg/m2 or the BCNU dose exceeds approximately 200 mg/m2 or if the patient has, or is expected to have, prolonged bone marrow suppression following the drug treatment. (This applies to all embodiments of the present invention in which BCNU and/or melphalan are used.) The stem cells are collected prior to the administration of the chemotherapy drugs (e.g., melphalan), and are purified and stored. The bone marrow stem cells are preferably infused 1-2 days after the chemotherapy drugs. However, the stem cells can be administered at later times. Purified autologous bone marrow stem cells are strongly preferred. However, allogeneic bone marrow stem cells can also be employed. The use of purified stem cell preparations enriched for CD34+ hematopoietic cells and depleted of circulating tumor cells is preferred. Non-purified bone marrow stem cells can also be used.

Melphalan Dosing and Administration

In preferred embodiments of E2 and Ee2, the melphalan is in dose ranges of approximately 25 to 50 mg/m2, 50 to 75 mg/m2, 75 to 100 mg/m2, 100 to 150 mg/m2, and 10 to 200 mg/m2. In preferred embodiments, the melphalan dose is approximately 5, 10, 20, 30, 40, 50, 60, 70, 80, 90, 100, 110, 120, 130, 140, 150, 160, 170, 180, 190, and 200 mg/m2. The melphalan is administered IV over a period of approximately 5 to 60 minutes, although longer times can be employed if steps are taken so that the melphalan is not degraded in the IV solution prior to administration. The melphalan is administered either immediately before, concomitantly with, or immediately after the BCNU, hydroxocobalamin, and ascorbic acid. In preferred embodiments, the melphalan, BCNU, hydroxocobalamin, and ascorbic acid are all administered within a 6 hour, 5 hour, 4 hour, 3 hour, 2 hour, and 1 hour time period.

BCNU Dosing and Administration

In preferred embodiments of E2 and Ee2, the BCNU dose is approximately 50 to 400 mg/m2, 50 to 75 mg/m2, 75 to 125 mg/m2, 125 to 200 mg/m2, and 200 to 400 mg/m2. In preferred embodiments, the BCNU dose is approximately 50, 75, 100, 125, 150, 175, 200, 225, 250, 275, 300, 325, 350, 375, and 400 mg/m2. The BCNU is administered IV at a rate of approximately 3 mg/m2/min. The BCNU can be administered before, concurrently, or immediately after the melphalan. The BCNU is preferably administered before the ascorbic acid.

Ethanol Dosing and Administration

In embodiments of E2 and Ee2, the ethanol dose is in the ranges of approximately 0.5 to 40 grams, 500 mg to 3 grams/m2, 3 to 6 grams/m2, and 6 to 12 grams/m2. In preferred embodiments, the ethanol dose is approximately, 0.5, 1, 2, 4, 6, 8, 10, 12, 15, 20, 25, 30, 35, and 40 grams. The ethanol can be given orally or IV. When given intravenously the ethanol is given over approximately 30 minutes to 6 hours, depending upon the dose. The timing of the ethanol administration is before or concomitant with the administration of the ascorbic acid such that ethanol is present in the blood during the time of ascorbic acid exposure and hydrogen peroxide formation. In a preferred embodiment, the ethanol is given at the time of BCNU administration within a 1 hour period of ascorbic acid administration.

Hydroxocobalamin Dosing and Administration

In preferred embodiments of E2 and Ee2 the hydroxocobalamin dose is in the ranges of approximately 50 to 40,000 mg, 50 to 500 mg, 500 to 1000 mg, 1 to 3 grams and 3 to 10 grams. In other preferred embodiments, the hydroxocobalamin dose is approximately 50 mg, 100 mg, 250 mg, 500 mg, and 1, 2, 3, 4, 5, 6, 7, 8, 9, 10, 11, 12, 13, 14, 15, 16, 17, 18, 19, and 20 grams. In other preferred embodiments, the hydroxocobalamin dose is in the ranges of approximately 25 to 10,000 mg/m2, 25 to 250 mg/m2, 250 to 500 mg/m2, 0.5 to 1.5 grams/m2, and 1.5 to 5 grams/m2. In other preferred embodiments, the hydroxocobalamin dose is approximately 25 mg/m2, 50 mg/m2, 125 mg/m2, 250 mg/mg, and 0.5,1, 1.5, 2, 2.5, 3, 3.5, 4, 4.5, 5, 5.5, 6, 6.5, 7, 7.5, 8, 8.5, 9, 9.5, and 10 grams/m2. The hydroxocobalamin is administered IV over approximately 5 to 60 minutes. Both the hydroxocobalamin and ascorbic acid can be given simultaneously or essentially at the same time. Alternatively, the hydroxocobalamin can be given hours prior to the ascorbic acid, because hydroxocobalamin has a plasma half-life of approximately 26 to 31 hours. In a preferred embodiment, the hydroxocobalamin is given over approximately 10-15 minutes, immediately prior to the administration of the ascorbic acid, which is given over a time period of approximately 30-60 minutes.

Ascorbic Acid Dosing and Administration

In preferred embodiments of E2 and Ee2, the IV ascorbic acid dose is in the range of approximately, 1 to 3 grams/m2, 3 to 6 grams/m2, 6 to 12 grams/m2, 12 to 25 grams/m2, and 0.5 to 90 grams/m2. In preferred embodiments, the dose of ascorbic acid is approximately, 0.5, 1, 2, 5, 10, 15, 20, 25, 30, 35, 40, 50, 60, 70, 80, 90, 100, 125, and 150 grams. The ascorbic acid is given intravenously over approximately 5 to 360 minutes. In preferred embodiments, the ascorbic acid is given over approximately 5, 10, 15, 20, 25, 30, 35, 40, 45, 50, 55, 60, 70, 80, 90, 100, 120, 140, 160, 180, and 360 minutes.

Timing of Drug Administration

In preferred embodiments of E2 and Ee2, the melphalan, BCNU, ethanol, hydroxocobalamin, and ascorbic acid are all administered within a time period of approximately 6 hours. The drugs can also be given as split doses within the time period. In preferred embodiments, the time period is approximately 60, 90, 120, 150, 180, 210, 240, 300, or 360 minutes, 2 days before the bone marrow stem cell infusion (i.e., on day minus 2, where day 0 is the day of stem cell infusion.)

Nomenclature Used to Label Embodiments

For the sake of simplicity and economy of space, embodiments referring to specific doses of multiple drugs and specific types of metastatic cancers are uniquely specified with the nomenclature rules described below:
I. "En" refers to the method of treating cancer described in embodiment number n. For example, E2 refers to the methods of embodiment E2.
II. "Een" refers to the set of drugs described in embodiment Een. For example, Ee2 refers to the set of drugs described in embodiment Ee2.
III. "EnS" and "EenS" refer to embodiments En and Een in which stem cells are infused. Note that a lack of an "S" suffix does not imply that stem cells are not infused.
IV. "En(ABCDFTUM)" and "Een(ABCDFTUM)" refer respectively to embodiments En and Een, wherein:
   a) the dose of melphalan is given by the value of "A",
   b) the dose of BCNU is given by "B",
   c) the dose of ethanol is given by "C",
   d) the dose of hydroxocobalamin is given by "D",
   e) the dose of ascorbic acid is given by "F"
   f) the type of cancer is given by "TUM" as described below.
V. "A", "B", "C", "D", "F", "T", "U" and "M" are numbers equal to 0, 1, 2, 3, or 4.
VI. "ABCDFTUM" is a number in base 5. Base 5 is the mathematical system in which the individual numbers or digits are limited to 0, 1, 2, 3, and 4 in the positional numbering system. By contrast, base 10 is the standard numbering system with individual numbers 1, 2, 3, 4, 5, 6, 7, 8, and 9. Counting in base 5 is well known to one skilled in the art. The following reference relates to this matter and is hereby incorporated in its entirety by reference: Oxford Users' Guide to Mathematics Edited by Eberhard Zeidler, Oxford University Press, Oxford, UK. Page 227.
VII. "A" refers to the approximate dose of melphalan, wherein A=0 means the melphalan dose is 25 to 50 mg/m2, A=1 means 50 to 75 mg/m2, A=2 means 75 to 100 mg/m2, A=3 means 100 to 150 mg/m2, and A=4 means 10 to 200 mg/m2.
VIII. "B" refers to the approximate dose of BCNU; wherein B=0 means the dose is 50 to 75 mg/m2, B=1 means 75 to 125 mg/m2, B=2 means 125 to 200 mg/m2, B=3 means 200 to 400 mg/m2, and B=4 means 50-400 mg/m2.
IX. "C" refers to the approximate dose of ethanol; wherein C=0 means no ethanol, C=1 means the dose of ethanol is 500 mg to 3 grams/m2, C=2 means 3 to 6 grams/m2, C=3 means 6 to 12 grams/m2, C=4 means 500 mg to 40 grams/m2
X. "D" refers to the approximate dose of hydroxocobalamin; wherein D=0 means the dose is 25 to 250 mg/m2; D=1 means 250 to 500 mg/m2, D=2 means 0.5 to 1.5 grams/m2; D=3 means 1.5 to 5 grams/m2, and D=4 means 25 to 20,000 mg/m2 of hydroxocobalamin.
XI. "F" refers to the approximate dose of ascorbic acid; wherein F=0 means the dose is 1 to 3 grams/m2, F=1 means 3 to 6 grams/m2, F=2 means 6 to 12 grams/m2, F=3 means 12 to 25 grams/m2, and F=4 means 0.5 to 90 grams/m2.
XII. "TUM" refers to the type of metastatic cancer or tumor, wherein when TUM has the values listed below, the metastatic cancer types that can be treated with the embodiment are as indicate below.
TUM=000 Metastatic cancer
TUM=001 Refractory metastatic cancer TUM=002 BRCA1-related metastatic cancer (inherited mutation)
TUM=003 BRCA2-related metastatic cancer (inherited mutation)
TUM=004 PALB2-related metastatic cancer (inherited mutation)
TUM=010 Metastatic cancer in the setting of an inherited BRCA/Fanconi pathway mutation(s)
TUM=011 Metastatic cancer in the setting of an acquired tumor cell mutation in BRCA/Fanconi pathway mutation(s)
TUM=012 BRCA2-related pancreatic cancer (inherited mutation)
TUM=013 BRCA2-related prostate cancer (inherited mutation)
TUM=014 BRCA2-related ovarian cancer (inherited mutation)
TUM=020 BRCA2-related fallopian tube cancer (inherited mutation)
TUM=021 BRCA2-related breast cancer (inherited mutation)
TUM=022 BRCA1-related pancreatic cancer (inherited mutation)
TUM=023 BRCA1-related prostate cancer (inherited mutation)
TUM=024 BRCA1-related ovarian cancer (inherited mutation)
TUM=030 BRCA1-related fallopian tube cancer (inherited mutation)
TUM=031 BRCA1-related breast cancer (inherited mutation)
TUM=032 PALB2-related pancreatic cancer (inherited mutation)
TUM=033 PALB2-related prostate cancer (inherited mutation)
TUM=034 PALB2-related ovarian cancer (inherited mutation)
TUM=040 PALB2-related fallopian tube cancer (inherited mutation)
TUM=041 PALB2-related breast cancer (inherited mutation)
TUM=042 Breast cancer (ductal adenocarcinoma)
TUM=043 RAD50-related breast cancer (inherited mutation)
TUM=044 Cancers that arise in patients with an inherited germline mutation(s) and/or an acquired somatic mutation(s) in a gene(s) involved in DNA crosslink repair, homologous recombination, or DNA repair.
TUM=100 Breast cancer (lobular adenocarcinoma)
TUM=101 Breast cancer (sarcoma)
TUM=102 Breast cancer (triple negative)
TUM=103 Breast cancer (inflammatory)
TUM=104 Breast cancer (Paget's)
TUM=110 Prostate cancer (adenocarcinoma)
TUM=111 Pancreatic cancer (adenocarcinoma, Stage I-IV)
TUM=112 Ovarian cancer (serous)
TUM=113 Ovarian cancer (endometroid)
TUM=114 Ovarian cancer (clear cell)
TUM=120 Ovarian cancer (mucinous)
TUM=121 Adenocarcinomas
TUM=122 Basal cell carcinoma
TUM=123 Bile duct cancer
TUM=124 Bladder cancer
TUM=130 Bronchial cancer
TUM=131 Carcinoid tumor
TUM=132 Cervical cancer (squamous)
TUM=133 Cervical cancer (adenocarcinoma)
TUM=134 Colorectal cancer
TUM=140 Colon cancer
TUM=141 Duodenal cancer
TUM=142 Endometrial cancer
TUM=143 Endometroid endometrial cancer
TUM=144 Esophageal cancer
TUM=200 Esophageal cancer (squamous cell)
TUM=201 Esophageal cancer (adenocarcinoma)
TUM=202 Ewing sarcoma
TUM=203 Fallopian tube cancer
TUM=204 Ocular melanoma
TUM=210 Malignant fibrous histiocytoma of bone
TUM=211 Osteosarcoma
TUM=212 Gallbladder cancer
TUM=213 Gastric cancer
TUM=214 Gastrointestinal carcinoid tumor
TUM=220 Gastrointestinal stromal tumors (GIST)
TUM=221 Germ cell tumors
TUM=222 Head and neck cancer
TUM=223 Hepatocellular cancer
TUM=224 Hypopharyngeal cancer
TUM=230 Malignant islet cell tumors
TUM=231 Pancreatic Neuroendocrine Tumors
TUM=232 Renal cell carcinoma
TUM=233 Laryngeal cancer
TUM=234 Lip and oral cavity cancer
TUM=240 Leiomyosarcomas
TUM=241 Lymphoma
TUM=242 Leukemia
TUM=243 T cell leukemia
TUM=244 B-cell lymphoma
TUM=300 B-cell leukemia
TUM=301 Acute myelogenous leukemia
TUM=302 Myeloma
TUM=303 Non-Hodgkins lymphoma
TUM=304 Lung cancer
TUM=310 Non-small cell lung cancer
TUM=311 Small cell lung cancer
TUM=312 Lung cancer (adenocarcinoma)
TUM=313 Lung cancer (large cell)
TUM=314 Lung cancer (squamous cell)
TUM=320 Melanoma
TUM=321 Merkel cell carcinoma
TUM=322 Mesothelioma
TUM=323 Nasal cavity and paranasal sinus cancer
TUM=324 Nasopharyngeal cancer
TUM=330 Neuroendocrine cancer
TUM=331 Oral cancer
TUM=332 Oropharyngeal cancer
TUM=333 Pancreatic neuroendocrine tumors
TUM=334 Paranasal sinus and nasal cavity cancer
TUM=340 Parathyroid cancer
TUM=341 Penile cancer
TUM=342 Pharyngeal cancer
TUM=343 Pheochromocytoma
TUM=344 Rectal cancer
TUM=400 Renal cell cancer
TUM=401 Renal clear cell cancer
TUM=402 Renal chromophobe cancer
TUM=403 Renal papillary cancer
TUM=404 Renal pelvis and ureter
TUM=410 Transitional cell cancer
TUM=411 Salivary gland cancer
TUM=412 Sarcomas
TUM=413 Squamous cell carcinomas
TUM=414 Osteosarcoma
TUM=420 Rhabdomyosarcoma TUM=421 Merkel cell carcinoma
TUM=422 Small intestine cancer
TUM=423 Soft tissue sarcoma
TUM=424 Squamous cell carcinoma
TUM=430 Squamous neck cancer with occult primary
TUM=431 Testicular cancer
TUM=432 Thyroid cancer (papillary, follicular, medullary, and anaplastic)
TUM=433 Transitional cell cancer of the renal pelvis and ureter
TUM=434 Urethral cancer
TUM=440 Uterine cancer
TUM=441 Undifferentiated cancer
TUM=442 Endometrial Uterine Sarcoma
TUM=443 Vaginal cancer
TUM=444 Vulvar cancer Examples of Using The Nomenclature a) E2(12212012) refers to embodiment E2, in which ABCDFTUM=12212012, which means A=1, B=2, C=2, D=1 and F=2, and TUM=012, which means the embodiment of E2 in which the melphalan dose (A=1) is 50 to 75 mg/m2, the BCNU dose (B=2) is 125 to 200 mg/m2, the ethanol dose (C=2) is 3 to 6 grams/m2, the hydroxocobalamin dose (D=1) is 250 to 500 mg/m2, the ascorbic acid dose (F=2) is 6 to 12 grams/m2, and the metastatic cancer (TUM=012) is pancreatic cancer in the setting of an inherited BRCA2 mutation.
b) E2S(12212012) refers to the above embodiment E2(12212012) in which stem cells are infused.
c) Ee2(12222013) refers to embodiment Ee2, in which ABCDFTUM=12222013, which means A=1, B=2, C=2, D=2 and F=2, and TUM=013, which means the embodiment of Ee2 in which the melphalan dose (A=1) is 50 to 75 mg/m2, the BCNU dose (B=2) is 125 to 200 mg/m2, the ethanol dose (C=2) is 3 to 6 grams/m2, the hydroxocobalamin dose (D=2) is 0.5 to 1.5 grams/m2, the ascorbic acid dose (F=2) is 6 to 12 grams/m2, and the metastatic cancer (TUM=013) is prostate cancer in the setting of an inherited BRCA2 mutation.
d) Ee2S(12222013) refers to the above embodiment Ee2 (12222013) in which stem cells are infused.

Additional Embodiments of E2 and E2S

Using the above nomenclature, some additional embodiments of E2 and E2S are E2(ABCDFTUM) and E2S(ABCDFTUM) where ABCDFTUM=00000000, 00000001, 00000002, 00000003, 00000004, 00000010, 00000011, 00000012, . . . , 44444444. To save space, the ellipsis is used to represent all the intervening numbers in the sequence. In other words, ABCDFTUM =00000000 to 44444444 sequentially in base 5. Therefore, a list of some embodiments of E2 is: E2(00000000), E2(00000001), E2(00000002), E2(00000003), E2(00000004), E2(00000010), E2(00000011), E2(00000012), E2(00000013), E2(00000014), E2(00000020), . . . , E2(44444444). Similarly, a list of some embodiments of E2S is E2S(00000000), E2S(00000001), E2S(00000002), E2S(00000003), E2S (00000004), E2S(00000010), E2S(00000011), E2S (00000012), E2S(00000013), E2S(00000014), E2S (00000020), . . . , E2S(44444444).

Additional Embodiments of Ee2 and Ee2S

A list of some embodiments of Ee2 is: Ee2(00000000), Ee2(00000001), Ee2(00000002), Ee2(00000003), Ee2 (00000004), Ee2(00000010), Ee2(00000011), Ee2 (00000012), Ee2(00000013), Ee2(00000014), Ee2 (00000020), . . . , Ee2(44444444). A list of some embodiments of Ee2S is: Ee2S(00000000), Ee2S (00000001), Ee2S(00000002), Ee2S(00000003), Ee2S (00000004), Ee2S(00000010), Ee2S(00000011), Ee2S (00000012), Ee2S(00000013), Ee2S(00000014), Ee2S (00000020), . . . , Ee2S(44444444).

Embodiment E3 (Treatment)

E3 is a method for the treatment of metastatic cancer in a subject, comprising administering a combination of 1,3-bis (2-chloroethyl)-1-nitrosourea, melphalan, hydroxocobalamin and ascorbic acid, simultaneously or within a six-hour time period, and optionally administering ethanol and optionally administering stem cells.

Embodiment Ee3 (Treatment)

Ee3 is a set of drugs or kit comprising 1,3-bis(2-chloroethyl)-1-nitrosourea, melphalan, hydroxocobalamin, and ascorbic acid, for use in a regimen for the treatment of metastatic cancer; wherein the regimen comprises administering the drugs simultaneously or within a six-hour time period, and optionally administering ethanol and optionally administering stem cells.

Additional Embodiments of E3, E3S, Ee3 and Ee3S

A list of some embodiments of E3 is: E3(00000000), E3(00000001), E3(00000002), E3(00000003), E3(00000004), E3(00000010), E3(00000011), E3(00000012), E3(00000013), E3(00000014), E3(00000020), . . . , E3(44444444). A list of some embodiments of E3S is: E3 S(00000000), E3 S(00000001), E3 S(00000002), E3 S(00000003), E3 S(00000004), E3 S(00000010), E3 S(00000011), E3 S(00000012), E3 S(00000013), E3 S(00000014), E3 S(00000020), . . . , E3S(44444444). A list of some embodiments of Ee3 is: Ee3(00000000), Ee3(00000001), Ee3(00000002), Ee3 (00000003), Ee3(00000004), Ee3 (00000010), Ee3 (00000011), Ee3 (00000012), Ee3 (00000013), Ee3 (00000014), Ee3(00000020), . . . , Ee3(44444444). A list of some embodiments of Ee3S is: Ee3 S(00000000), Ee3 S(00000001), Ee3 S(00000002), Ee3 S(00000003), Ee3 S(00000004), Ee3 S(00000010), Ee3 S(00000011), Ee3 S(00000012), Ee3 S(00000013), Ee3 S(00000014), Ee3 S(00000020), . . . , Ee3S(44444444).

Embodiment E4 (Effective Treatment)

E4 is a method for the effective treatment of metastatic cancer in a subject, comprising administering a combination of 1,3-bis(2-chloroethyl)-1-nitrosourea, melphalan, hydroxocobalamin, and ascorbic acid, simultaneously or within a six-hour time period, and optionally administering ethanol and optionally administering stem cells.

Embodiment Ee4 (Effective Treatment)

Ee4 is a set of drugs or kit comprised of 1,3-bis(2-chloroethyl)-1-nitrosourea, melphalan, hydroxocobalamin, and ascorbic acid, for use in a regimen for the effective treatment of metastatic cancer; wherein the regimen comprises administering the drugs simultaneously or within a six-hour time period, and optionally administering ethanol and optionally administering stem cells.

Additional Embodiments of E4, E4S, Ee4 and Ee4S

A list of some embodiments of E4 is: E4(00000000), E4(00000001), E4(00000002), E4(00000003), E4(00000004), E4(00000010), E4(00000011), E4(00000012), E4(00000013), E4(00000014), E4(00000020), . . . , E4(44444444). A list of some embodiments of E4S is: E4S(00000000), E4S(00000001), E4S (00000002), E4S(00000003), E4S(00000004), E4S (00000010), E4S(00000011), E4S(00000012), E4S (00000013), E4S(00000014), E4S(00000020), . . . , E4S (44444444). A list of some embodiments of Ee4 is: Ee4 (00000000), Ee4(00000001), Ee4(00000002), Ee4 (00000003), Ee4(00000004), Ee4(00000010), Ee4 (00000011), Ee4(00000012), Ee4(00000013), Ee4 (00000014), Ee4(00000020), . . . , Ee4(44444444). A list of some embodiments of Ee4S is: Ee4S(00000000), Ee4S (00000001), Ee4S(00000002), Ee4S(00000003), Ee4S (00000004), Ee4S(00000010), Ee4S(00000011), Ee4S (00000012), Ee4S(00000013), Ee4S(00000014), Ee4S (00000020), . . . , Ee4S(44444444).

Embodiment E5 (Effective Treatment, Refractory Metastatic Cancers)

E5 is a method for the effective treatment of refractory metastatic cancer in a subject, comprising administering a combination of 1,3-bis(2-chloroethyl)-1-nitrosourea, melphalan, hydroxocobalamin, and ascorbic acid, simultaneously or within a six-hour time period, and optionally administering ethanol and optionally administering stem cells.

Embodiment Ee5 (Effective Treatment, Refractory Metastatic Cancer)

Ee5 is a set of drugs or kit comprising 1,3-bis(2-chloroethyl)-1-nitrosourea, melphalan, hydroxocobalamin, and ascorbic acid, for use in a regimen for the effective treatment of refractory metastatic cancer; wherein the regimen comprises administering the drugs simultaneously or within a six-hour time period, and optionally administering ethanol and optionally administering stem cells.

Additional Embodiments of E5, ESS, Ee5 and Ee5S

A list of some embodiments of E5 is: E5(00000000), E5(00000001), E5(00000002), E5(00000003), E5(00000004), E5(00000010), E5(00000011), E5(00000012), E5(00000013), E5(00000014), E5(00000020), . . . , E5(44444444). A list of some embodiments of E5S is: E5S(00000000), E5S(00000001), E5S (00000002), E5S(00000003), E5S(00000004), E5S (00000010), E5S(00000011), E5S(00000012), E5S (00000013), E5S(00000014), E5S(00000020), . . . , E5S (44444444). A list of some embodiments of Ee5 is: Ee5 (00000000), Ee5(00000001), Ee5(00000002), Ee5 (00000003), Ee5(00000004), Ee5(00000010), Ee5 (00000011), Ee5(00000012), Ee5(00000013), Ee5 (00000014), Ee5(00000020), . . . , Ee5(44444444). A list of some embodiments of Ee5S is: Ee5S(00000000), Ee5S (00000001), Ee5S(00000002), Ee5S(00000003), Ee5S (00000004), Ee5S(00000010), Ee5S(00000011), Ee5S (00000012), Ee5S(00000013), Ee5S(00000014), Ee5S (00000020), . . . , EeSS(44444444).

Some Preferred Embodiments of E1-E5 and Ee1-Ee5

In some preferred embodiments of E1 and Ee1, and E2S and Ee2S, and E3S and Ee3S, and E4S and Ee4S, and E5S and EeSS, the drug doses are as given below:

i. Melphalan 75 to 100 mg/m2, BCNU 125 to 200 mg/m2, ethanol 3 to 6 grams/m2, hydroxocobalamin 0.5 to 1.5 grams/m2, and ascorbic acid 3 to 6 grams/m2.
ii. Melphalan 75 to 100 mg/m2, BCNU 125 to 200 mg/m2, ethanol 3 to 6 grams/m2, hydroxocobalamin 0.5 to 1.5 grams/m2, and ascorbic acid 6 to 12 grams/m2.
iii. Melphalan 75 to 100 mg/m2, BCNU 125 to 200 mg/m2, ethanol 3 to 6 grams/m2, hydroxocobalamin 0.5 to 1.5 grams/m2, and ascorbic acid 12 to 25 grams/m2.
iv. Melphalan 75 to 100 mg/m2, BCNU 75 to 125 mg/m2, ethanol 3 to 6 grams/m2, hydroxocobalamin 0.5 to 1.5 grams/m2, and ascorbic acid 3 to 6 grams/m2.
v. Melphalan 75 to 100 mg/m2, BCNU 75 to 125 mg/m2, ethanol 3 to 6 grams/m2, hydroxocobalamin 0.5 to 1.5 grams/m2, and ascorbic acid 6 to 12 grams/m2.
vi. Melphalan 75 to 100 mg/m2, BCNU 75 to 125 mg/m2, ethanol 3 to 6 grams/m2, hydroxocobalamin 0.5 to 1.5 grams/m2, and ascorbic acid 12 to 25 grams/m2.
vii. Melphalan 50 to 75 mg/m2, BCNU 125 to 200 mg/m2, ethanol 3 to 6 grams/m2, hydroxocobalamin 0.5 to 1.5 grams/m2, and ascorbic acid 3 to 6 grams/m2.
viii. Melphalan 50 to 75 mg/m2, BCNU 125 to 200 mg/m2, ethanol 3 to 6 grams/m2, hydroxocobalamin 0.5 to 1.5 grams/m2, and ascorbic acid 6 to 12 grams/m2.
ix. Melphalan 50 to 75 mg/m2, BCNU 125 to 200 mg/m2, ethanol 3 to 6 grams/m2, hydroxocobalamin 0.5 to 1.5 grams/m2, and ascorbic acid 12 to 25 grams/m2.
x. Melphalan 50 to 75 mg/m2, BCNU 75 to 125 mg/m2, ethanol 3 to 6 grams/m2, hydroxocobalamin 0.5 to 1.5 grams/m2, and ascorbic acid 3 to 6 grams/m2.
xi. Melphalan 50 to 75 mg/m2, BCNU 75 to 125 mg/m2, ethanol 3 to 6 grams/m2, hydroxocobalamin 0.5 to 1.5 grams/m2, and ascorbic acid 6 to 12 grams/m2.
xii. Melphalan 50 to 75 mg/m2, BCNU 75 to 125 mg/m2, ethanol 3 to 6 grams/m2, hydroxocobalamin 0.5 to 1.5 grams/m2, and ascorbic acid 12 to 25 grams/m2.
xiii. Melphalan 100 to 150 mg/m2, BCNU 125 to 200 mg/m2, ethanol 3 to 6 grams/m2, hydroxocobalamin 0.5 to 1.5 grams/m2, and ascorbic acid 3 to 6 grams/m2.
xiv. Melphalan 100 to 150 mg/m2, BCNU 125 to 200 mg/m2, ethanol 3 to 6 grams/m2, hydroxocobalamin 0.5 to 1.5 grams/m2, and ascorbic acid 6 to 12 grams/m2.
xv. Melphalan 100 to 150 mg/m2, BCNU 125 to 200 mg/m2, ethanol 3 to 6 grams/m2, hydroxocobalamin 0.5 to 1.5 grams/m2, and ascorbic acid 12 to 25 grams/m2.
xvi. Melphalan 100 to 150 mg/m2, BCNU 75 to 125 mg/m2, ethanol 3 to 6 grams/m2, hydroxocobalamin 0.5 to 1.5 grams/m2, and ascorbic acid 3 to 6 grams/m2.
xvii. Melphalan 100 to 150 mg/m2, BCNU 75 to 125 mg/m2, ethanol 3 to 6 grams/m2, hydroxocobalamin 0.5 to 1.5 grams/m2, and ascorbic acid 6 to 12 grams/m2.
xviii. Melphalan 100 to 150 mg/m2, BCNU 75 to 125 mg/m2, ethanol 3 to 6 grams/m2, hydroxocobalamin 0.5 to 1.5 grams/m2, and ascorbic acid 12 to 25 grams/m2.
xix. Melphalan 150 to 200 mg/m2, BCNU 125 to 200 mg/m2, ethanol 3 to 6 grams/m2, hydroxocobalamin 0.5 to 1.5 grams/m2, and ascorbic acid 3 to 6 grams/m2.

xx. Melphalan 150 to 200 mg/m2, BCNU 125 to 200 mg/m2, ethanol 3 to 6 grams/m2, hydroxocobalamin 0.5 to 1.5 grams/m2, and ascorbic acid 6 to 12 grams/m2.
xxi. Melphalan 150 to 200 mg/m2, BCNU 125 to 200 mg/m2, ethanol 3 to 6 grams/m2, hydroxocobalamin 0.5 to 1.5 grams/m2, and ascorbic acid 12 to 25 grams/m2.
xxii. Melphalan 150 to 200 mg/m2, BCNU 75 to 125 mg/m2, ethanol 3 to 6 grams/m2, hydroxocobalamin 0.5 to 1.5 grams/m2, and ascorbic acid 3 to 6 grams/m2.
xxiii. Melphalan 150 to 200 mg/m2, BCNU 75 to 125 mg/m2, ethanol 3 to 6 grams/m2, hydroxocobalamin 0.5 to 1.5 grams/m2, and ascorbic acid 6 to 12 grams/m2.
xxiv. Melphalan 150 to 200 mg/m2, BCNU 75 to 125 mg/m2, ethanol 3 to 6 grams/m2, hydroxocobalamin 0.5 to 1.5 grams/m2, and ascorbic acid 12 to 25 grams/m2.

In some preferred embodiments of the above embodiments, the cancer is pancreatic, breast, ovarian, or prostate. In some preferred embodiments of the above embodiments, the cancer is in a subject with an inherited BRCA1 and/or BRCA2 mutation.

Embodiment E6

E6 is a method for the treatment of metastatic cancer or refractory metastatic cancer in a subject, comprising administering a combination of 1,3-bis(2-chloroethyl)-1-nitrosourea, melphalan, hydroxocobalamin, and ascorbic acid, simultaneously or within a six-hour time period; wherein the melphalan dose is in the range of 20 to 200 mg/m2.

In a preferred embodiment of E6, 1,3-bis(2-chloroethyl)-1-nitrosourea is administered at a dose range of 50 to 400 mg/m2; the melphalan is administered at a dose of 20 to 200 mg/m2; the hydroxocobalamin is administered at a dose of 25 to 20,000 mg/m2; and the ascorbic acid is administered a dose of 1 gram to 150 grams.

In a preferred embodiment of E6, the 1,3-bis(2-chloroethyl)-1-nitrosourea is administered at a dose range of 75 to 300 mg/m2; the melphalan is administered at a dose of 50 to 200 mg/m2; the hydroxocobalamin is administered at a dose of 400 to mg to 800 mg/m2; and the ascorbic acid is administered a dose of 5 grams to 40 grams.

In a preferred embodiment of E6, the 1,3-bis(2-chloroethyl)-1-nitrosourea is administered at a dose of 150 mg/m2; the melphalan is administered at a dose of 70-140 mg/m2; the hydroxocobalamin is administered at a dose of 580 mg/m2; and the ascorbic acid is administered a dose of 5 grams to 25 grams.

In preferred embodiments of the above E6 embodiments, the methods are further comprising systemically administering ethanol at a dose of 500 mg to 40 grams.

In preferred embodiments of the above E6 embodiments, the methods are further comprising bone marrow stem cell transplantation therapy.

In preferred embodiments of the above E6 embodiments, the methods are for the treatment for metastatic cancer in a subject with an inherited germline mutation in a gene involved in DNA repair, and/or homologous recombination, and or DNA crosslink repair.

In preferred embodiments of the above E6 embodiments, the methods are for the treatment for metastatic cancer in a subject with an inherited germline mutation in one or more of the following genes: ATR, BARD1, BLM, BRCA1, BRCA2, BRIP1 (FANCJ, BACH1), EME1, ERCC1, ERCC4, FAN1, FANCA, FANCB, FANCC, FANCD1, FANCD2, FANCE, FANCF, FANCG, FANCI, FANCJ, FANCL, FANCM, FANCN, FANCO, FANCP, FANCQ, FANCQ, FANCR, FANCS, FANCT, HELQ, MEN1, MUS81, NBN (NBS1), PALB2, RAD50, RAD51 (FANCR), RAD51C (FANCO), RAD51D, REV1, SLX4 (FANCP), UBE2T (FANCT), USP1, WDR48, XPF, XRCC2, and XRCC3.

In preferred embodiments of the above E6 embodiments, the methods are for the treatment for metastatic cancer in a subject with an inherited germline mutation in BRCA1 and/or BRCA2.

In preferred embodiments of the above E6 embodiments, the methods are for the treatment for metastatic cancer in a subject with one or more of the following types of cancer: pancreatic cancer, ovarian cancer, breast cancer, and prostate cancer.

Embodiment E7

E7 is a method for sensitizing cancer cells to DNA-damaging agents in vivo, comprising the administration of the DNA-damaging agent, a glutathione reductase inhibitor, hydroxocobalamin, and ascorbic acid. In a preferred embodiment of E7, the glutathione inhibitor is 1,3-bis(2-chloroethyl)-1-nitrosourea.

Embodiment E8

E8 is a method of treating cancer comprising the administration of 1,3-bis(2-chloroethyl)-1-nitrosourea, hydroxocobalamin, and ascorbic acid.

Embodiment E9

Embodiment E9 is a method for the selective delivery of one or more drugs to solid cancers for the treatment of cancer, where the method comprises:
a. Selecting two compounds referred to as Agent 1 and Agent 2; wherein Agent 1 and Agent 2 are not enzymes, and wherein said agents distribute into the extracellular space after systemic administration, and spontaneously react to directly or indirectly generate one or more drugs; wherein said drugs are rapidly decomposed, degraded, or otherwise eliminated or detoxified from the intravascular compartment; wherein said drugs rapidly efflux from the interstitial fluid and enter the intracellular fluid; and wherein said drugs exert a cancer treatment effect.
b. Systemically administering Agent 1 and Agent 2.

In a preferred embodiment of E9, Agent 1 is hydroxocobalamin and Agent 2 is ascorbic acid, and the drug is hydrogen peroxide or dehydroascorbic acid, or 2,3-diketogulonic acid.

Embodiment E10

Embodiment E10 is a set or kit of pharmaceutical compositions for use in effectively treating metastatic cancer or refractory metastatic cancer in a subject, comprising a therapeutically effective dose of a combination of 1,3-bis(2-chloroethyl)-1-nitrosourea, melphalan, hydroxocobalamin, and ascorbic acid.

Embodiment E11

Embodiment E11 comprises the use of a pharmaceutical composition for the treatment of metastatic cancer or refractory metastatic cancer in a subject, comprising a therapeutically effective dose of a combination of 1,3-bis(2-chloroethyl)-1-nitrosourea, melphalan, hydroxocobalamin and ascorbic acid, wherein the melphalan dose is in the range of 20 to 200 mg/m2.

Alternate Forms of the Active Principles

It will be appreciated that in the methods and compositions described herein, any suitable form of the active principles (e.g., drugs) may be used, e.g., a salt form, or a prodrug or active metabolite; these forms are within the scope of the present invention.

Melphalan Formulations

A preferred melphalan formulation comprises melphalan hydrochloride equivalent to 5 mg/ml of melphalan, 2 mg/ml of povidone, 20 mg/ml of sodium citrate, 6.0 ml of propylene glycol, 0.52 ml 96% ethanol, and water to give a volume of 10 ml, which is then diluted with 0.9% Sodium Chloride for intravenous Injection, USP, to give a melphalan concentration not greater than 0.45 mg/mL.

BCNU Formulation

A preferred BCNU formulation comprises of 100 mg of BCNU dissolved in 3 ml of 96% ethanol and 27 ml of Water for Intravenous Injection, USP, which is further diluted with 0.9% Sodium Chloride Injection, USP to a BCNU concentration of approximately 0.6 mg/ml.

Hydroxocobalamin Formulation

A preferred formulation comprises hydroxocobalamin dissolved in 0.9% Sodium Chloride for Intravenous Injection, USP at a concentration of not more than 25 mg/ml.

Ascorbic Acid Formulations

A preferred formulation of ascorbic acid comprises ascorbic acid and an equimolar amount of sodium hydroxide with the pH adjusted to approximately 5 to 7 (with sodium hydroxide or sodium bicarbonate), which is diluted in Water for Intravenous Injection, USP, to give a final concentration of 25 mg/ml of ascorbic acid, which is isotonic with an osmolarity of ~280 mOsm/L. In other preferred formulations, the solution can be more concentrated with the ascorbic acid concentration ranging up to 80 mg/ml. Hypertonic solutions need to be given by a central IV line.

Formulation, Administration Techniques, and Dosage Forms

In certain embodiments, the pharmaceutical compositions described herein are formulated as a form suitable for oral administration, as a tablet, as a capsule, as a cachet, as a pill, as a lozenge, as a powder, or as a granule. In some embodiments of the present invention, the pharmaceutical compositions are formulated as sustained release formulations, solutions, liquids, or suspensions; for parenteral injection as a sterile solution, suspension or emulsion; for topical administration as an ointment, cream, lotion, spray, foam, gel, or paste; or for rectal or vaginal administration as a suppository or pessary. In certain embodiments, the pharmaceutical compositions are formulated in unit dosage forms suitable for single administration of precise dosages. In certain aspects, the pharmaceutical composition includes a conventional pharmaceutical carrier or excipient and an agent as described herein as an active ingredient. In addition, other medicinal or pharmaceutical agents, carriers, adjuvants, etc. are included. Exemplary parenteral administration forms include solutions or suspensions of active agents in sterile aqueous solutions, for example, aqueous propylene glycol or dextrose solutions. Such dosage forms are optionally buffered.

Suitable pharmaceutical carriers include inert diluents or fillers, water, and various organic solvents. The pharmaceutical compositions optionally contain additional ingredients such as flavorings, binders, excipients, and the like. For example, in a specific embodiment, tablets containing various excipients, such as citric acid, are employed together with various disintegrants. Additionally, lubricating agents such as magnesium stearate, sodium lauryl sulfate, and talc are optionally used. Other reagents such as an inhibitor, surfactant or solubilizer, plasticizer, stabilizer, viscosity increasing agent, or film-forming agent are also optionally added. In certain embodiments, solid compositions of a similar type are employed in soft or hard filled gelatin capsules. In certain embodiments, the pharmaceutical compositions and/or formulations described herein include lactose or milk sugar or high molecular weight polyethylene glycols. When aqueous suspensions or elixirs are desired for oral administration, the active ingredient or ingredients are optionally combined with various sweetening or flavoring agents, coloring agents or dyes or, emulsifying agents or suspending agents, together with diluents such as water, ethanol, propylene glycol, glycerin, or combinations thereof. Those of ordinary skill in the art are familiar with formulation and administration techniques that can be employed with the agents and methods of the invention, e.g., as discussed in Goodman and Gilman, The Pharmacological Basis of Therapeutics (current edition), McGraw-Hill; and Remington's, Pharmaceutical Sciences (current edition), Mack Publishing Co., Easton, Pa. Formulations for parenteral administration include aqueous and non-aqueous (oily) sterile injection solutions of the active agents, which may contain antioxidants, buffers, biocide, bacteriostats and solutes that render the formulation isotonic with the blood of the intended recipient; and aqueous and non-aqueous sterile suspensions which optionally include suspending agents or thickening agents. Examples of suitable isotonic vehicles for use in such formulations include sodium chloride injection, Ringer's solution, or lactated Ringer's injection. Suitable lipophilic solvents or vehicles include fatty oils such as sesame oil, or synthetic fatty acid esters such as ethyl oleate or triglycerides; or liposomes or other microparticulate systems may be used to target the agent to blood components or one or more organs. The concentration of the active ingredient or ingredients in the solution varies depending on intended usage. Non-limiting examples of excipients that are used in conjunction with the present invention include water, saline, dextrose, glycerol, or ethanol. The injectable compositions optionally comprise minor amounts of non-toxic auxiliary substances such as wetting or emulsifying agents, pH buffering agents, stabilizers, solubility enhancers, or other such agents such as sodium acetate, sorbitan monolaurate, triethanolamine oleate or cyclodextrins. Drugs that have acidic or basic groups may be administered in formulations as pharmacologically acceptable salts; for example, melphalan may administered as melphalan hydrochloride, and ascorbic acid may be administered as sodium ascorbate. Examples of pharmaceutically acceptable carriers that are optionally used include aqueous vehicles, nonaqueous vehicles, antimicrobial agents, isotonic agents, buffers, antioxidants, local anesthetics, suspending and dispersing agents, emulsifying agents, sequestering or chelating agents, and other pharmaceutically acceptable substances.

Additional Therapeutic Agents

The methods and compositions described herein can also further include additional therapeutic agents and drugs for the treatment of the cancer or for alleviating symptoms.

Antiemetic Drugs

The drugs combinations employed in the present methods have high potential to cause nausea and emesis. Effective methods to control these side effects are known to one skilled in the art and would be employed in conjunction with the current methods. Generally, patients would be pre-treated with dexamethasone and a serotonin antagonist. Suitable protocols are known to one skilled in the art. The following references relate to this matter: Guideline update for MASCC and ESMO in the prevention of chemotherapy- and radiotherapy-induced nausea and vomiting: results of the Perugia consensus conference. Roila F; et al; ESMO/MASCC Guidelines Working Group, Ann Oncol., 2010 May, 21 Suppl 5: v232-43.

EXAMPLES

Example 1

A patient with metastatic pancreatic cancer with an inherited BRCA2 mutation would be treated with the following protocol:
1. The patient would be screened to rule out underlying medical conditions that would preclude the treatment and stem cell therapy; such conditions would include serious infectious or heart, kidney, liver, metabolic, neurologic, hematologic, or lung diseases. In addition, the patient would be screened for drug contraindications that would preclude the treatment and stem cell therapy.

Stem cell mobilization, collection, purification, and storage:
2. Treatment with Neupogen 10 microgram/kg subcutaneously daily each morning for at least 4 days prior to planned start of apheresis and daily while undergoing apheresis. Techniques for using Neupogen are described in the FDA-approved package label.
3. Sufficient CD34+ cells would be collected by apheresis for 2-3 stem cell infusions and one reserve (i.e., greater than ~2×10^6 cells/kg/infusion).
4. If needed Plerixafor could be used to increase stem cell mobilization and yield. Techniques for using this drug are described in the Plerixafor FDA approved package label.
5. The CD34+ stem cells would be purified using CliniMacs™ technology and stored frozen until used.

Drug treatment: (day minus 2)
6. IV Hydration and antiemetic premedication prior to chemotherapy
7. Dexamethasone, 12 mg IV, 30 minutes prior to the chemotherapy
8. Palonosetron (Aloxi) 0.25 mg IV, 30 minutes prior to the chemotherapy
9. Aprepitant (EMEND) 125 mg orally, 1 hour prior to the chemotherapy
10. Melphalan: 90 mg/m2 IV over 15 minutes by a central line beginning at t=0 minutes
11. BCNU 150 mg/m2 IV and ethanol 3.5 grams/m2 over 50 minutes, beginning at t=15 minutes by a central line
12. Hydroxocobalamin, 525 mg/m2 IV over 15 minutes, immediately after completion of BCNU infusion
13. Ascorbic acid: 5800 mg/m2 over 30 minutes beginning at t=70 minutes
14. IV hydration for 24 hours, approximately 2 to 3 liters/m2/day Day Before Stem Cell Infusion: (day minus 1)
15. Dexamethasone 8 mg PO
16. Aprepitant 80 mg PO Stem Cell Infusion: (day 0)
17. Dexamethasone 8 mg PO
18. Aprepitant 80 mg PO
19. Stem cell infusion, at least 2×106 CD34+ cells/kg IV by central line Supportive Care:
20. Pegfilgrastim 6 mg subcutaneously, day+2
21. Conventional supportive therapy post stem cell transplantation, as needed, including platelet transfusion, RBC transfusion, and prophylactic antibiotics (e.g., Cipro), prophylactic acyclovir and other supportive care.

Next treatment cycle:
1 22. Repeat steps 6-21 in approx. 4-8 weeks for a total of 2-3 courses of melphalan, BCNU, ethanol, hydroxocobalamin, ascorbic acid, and stem cell infusions.

Example 2

In example 2, the treatment is as described in Example 1, however the melphalan is administered at a dose of 70 mg/m2 and the ascorbic acid dose is 11,600 mg/m2 over 45 minutes.

Example 3

In example 3, the treatment is as described in Example 1, the patient has metastatic prostate cancer in the setting of an inherited BRCA2 mutation. However, the melphalan is administered at a dose of 110 mg/m2.

Example 4

In example 3, the treatment is as described in Example 1, However, the BCNU dose is administered at a dose of 100 mg/m2.

Example 5

In example 5, the treatment is as described in Example 1, However, the patient has pancreatic cancer and does not have a BRCA mutation.

The same methods in the above examples could be used for patients with a wide range of metastatic BRCA-related and BRCA independent cancers, including but not limited to pancreatic cancer, prostate cancer, Stage IV breast cancer, platinum-resistant ovarian cancer, and the other types of cancers given in List A in this application.

The teachings of all patents, published applications, and references cited herein are incorporated by reference in their entirety. While this invention has been particularly shown, and described with references to example embodiments thereof, it will be understood by those skilled in the art that various changes in form and details may be made therein without departing from the scope of the invention encompassed by the appended claims.

What is claimed is:

1. A method of treating metastatic solid cancers in a subject comprising administering 1,3-bis(2-chloroethyl)-1-nitrosourea, hydroxocobalamin, and ascorbic acid, or pharmaceutically acceptable salts of any of the foregoing.

2. A method of treating metastatic solid cancers in a subject, comprising administering a combination of 1,3-bis(2-chloroethyl)-1-nitrosourea, melphalan, hydroxocobalamin, and ascorbic acid, or pharmaceutically acceptable salts of any of the foregoing, concomitantly or over a period of time; wherein the melphalan dose is in the range of approximately 20 mg/m$^2$ to approximately 200 mg/m$^2$.

3. The method of claim 2, wherein the 1,3-bis(2-chloroethyl)-1-nitrosourea is administered at a dose range of approximately 50 mg/m$^2$ to approximately 400 mg/m$^2$; the hydroxocobalamin is administered at a dose of approximately 25 mg/m$^2$ to approximately 20,000 mg/m$^2$, and the ascorbic acid is administered a dose of approximately 0.5 g/m$^2$ to approximately 90 g/m$^2$.

4. The method of claim 2, wherein the melphalan is administered at a dose of approximately 90 mg/m$^2$.

5. The method of claim 3, wherein the 1,3-bis(2-chloroethyl)-1-nitrosourea is administered at a dose of approximately 150 mg/m$^2$.

6. The method of claim 3, wherein the hydroxocobalamin is administered at a dose of approximately 1.5 g/m$^2$.

7. The method of claim 3, wherein the ascorbic acid is administered at a dose of approximately 0.5 g/m$^2$ to approximately 10 g/m$^2$.

8. The method of claim 2, further comprising infusing bone marrow stem cells in the subject after administering the combination of 1,3-bis(2-chloroethyl)-1-nitrosourea, melphalan, hydroxocobalamin, and ascorbic acid, or pharmaceutically acceptable salts of any of the foregoing.

9. The method of claim 2, further comprising the systemic administration of ethanol at a dose of approximately 500 mg to approximately 40 grams.

10. The method of claim 2, wherein the metastatic solid cancer is in a subject with an inherited germline mutation in a gene involved in DNA repair, and/or homologous recombination, and or DNA crosslink repair.

11. The method of claim 2, wherein the metastatic solid cancer is in a subject with an inherited germline mutation in BRCA1 and/or BRCA2.

12. The method of claim 2, wherein the metastatic solid cancer is selected from pancreatic cancer, ovarian cancer, breast cancer, or prostate cancer.

* * * * *